United States Patent [19]
Moore et al.

[11] Patent Number: 5,945,315
[45] Date of Patent: Aug. 31, 1999

[54] METHOD FOR PRODUCING CRYPTOPHYCINS BY CULTIVATING A NOSTOC SP.

[75] Inventors: Richard E. Moore; Gregory M. L. Patterson, both of Honolulu, Hi.

[73] Assignee: University of Hawaii, Honolulu, Hi.

[21] Appl. No.: 08/743,506

[22] Filed: Nov. 4, 1996

Related U.S. Application Data

[63] Continuation of application No. 08/249,955, May 27, 1994, abandoned, which is a continuation-in-part of application No. 08/172,632, Dec. 21, 1993, abandoned.

[51] Int. Cl.$^6$ .......................... C12P 21/04; C12P 13/04; C12P 17/14; C12P 13/00
[52] U.S. Cl. ..................... 435/106; 435/71.1; 435/120; 435/128; 514/183; 514/478
[58] Field of Search ................... 435/71.1, 106, 435/120, 128; 514/183, 478

[56] References Cited

U.S. PATENT DOCUMENTS

| | | | |
|---|---|---|---|
| 4,845,085 | 7/1989 | Sesin ........................................ | 514/183 |
| 4,845,086 | 7/1989 | Sesin ........................................ | 514/183 |
| 4,868,208 | 9/1989 | Sesin et al. .............................. | 514/475 |
| 4,946,835 | 8/1990 | Hirsch et al. ............................ | 514/183 |

FOREIGN PATENT DOCUMENTS 2220657  1/1990  United Kingdom .

OTHER PUBLICATIONS

Spjut RW et al., Econ. Bot. 42(1):62–72 (1988).
Smith et al., "Cryptophycin: A New Antimicrotubule Agent Active Against Drug–Resistant Cells," Cancer Res. 54(14):3779–84 (1994).
Trimurtulu et al., "Total Structures of Cryptophycins, Potent Antitumor Depsipeptides from the Blue–Green Alga Nostoc sp. Strain GSV 224," J. Am. Chem. Soc. 116(11):4729–37 (1994).
Schwartz et al., "Pharmaceuticals from Cultured ALgae," J. Ind. Microbiol. 5(2–3):113–23 (1990).

*Primary Examiner*—Sandra E. Saucier
*Attorney, Agent, or Firm*—Stephen E. Reiter; Gray Cary Ware & Freidenrich, LLP; Stanley H. Kim

[57] ABSTRACT

The present invention provides novel cryptophycin compounds having the following structure:

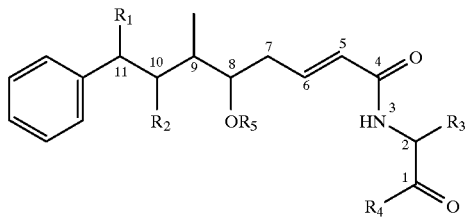

The present invention also provides methods for producing cryptophycins from the Nostoc sp. of blue-green algae (cyanobacteria). Pharmaceutical compositions comprising novel cryptophycins are also provided by the present invention, as are methods for using cryptophycins to inhibit the proliferation of hyperproliferative cells. The present invention further provides methods for using cryptophycins to inhibit the proliferation of hyperproliferative cells with drug resistant phenotypes, and to treat pathological conditions, such as neoplasia.

3 Claims, 4 Drawing Sheets

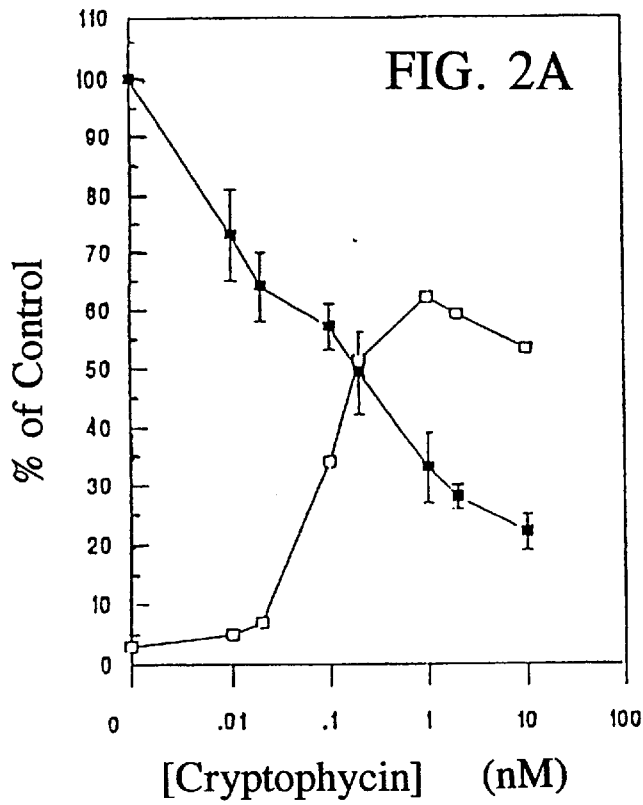
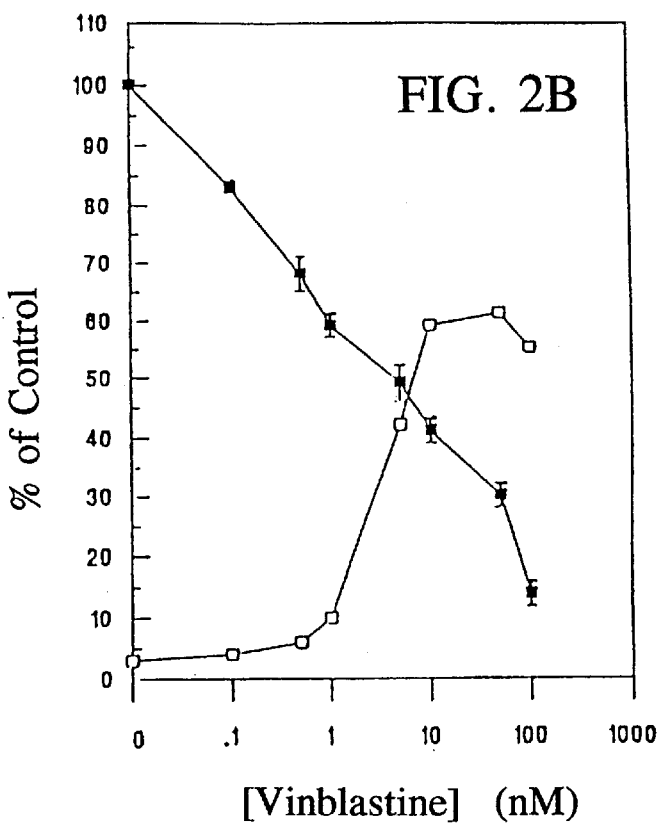

Time of Incubation (hr)

METHOD FOR PRODUCING CRYPTOPHYCINS BY CULTIVATING A NOSTOC SP.

This is a continuation of application Ser. No. 08/249,955, filed May 27, 1994, now abandoned which is a continuation-in-part of application Ser. No. 08/172,632, filed Dec. 21, 1993, now abandoned.

This invention was made in part with U.S. Government support under Grant No. CA12623 from The National Cancer Institute, Department of Health and Human Services. Accordingly, the U.S. Government may have certain rights in this invention.

BACKGROUND OF THE INVENTION

Neoplastic diseases, characterized by the proliferation of cells not subject to the normal control of cell growth, are a major cause of death in humans. Clinical experience in cancer chemotherapy has demonstrated that new and more effective drugs are desirable to treat these diseases. Such clinical experience has also demonstrated that drugs which disrupt the microtubule system of the cytoskeleton can be effective in inhibiting the proliferation of neoplastic cells.

The microtubule system of eukaryotic cells is a major component of the cytoskeleton and is in a dynamic state of assembly and disassembly; that is, heterodimers of tubulin are polymerized and form microtubule. Microtubules play a key role in the regulation of cell architecture, metabolism, and division. The dynamic state of microtubules is critical to their normal function. With respect to cell division, tubulin is polymerized into microtubules that form the mitotic spindle. The microtubules are then depolymerized when the mitotic spindle's use has been fulfilled. Accordingly, agents which disrupt the polymerization or depolymerization of microtubules, and thereby inhibit mitosis, comprise some of the most effective cancer chemotherapeutic agents in clinical use.

Such anti-mitotic agents or poisons may be classified into three groups on the basis of their molecular mechanism of action. The first group consists of agents, including colchicine and colcemid, which inhibit the formation of microtubules by sequestering tubulin. The second group consist of agents, including vinblastine and vincristine, which induce the formation of paracrystalline aggregates of tubulin.

Vinblastine and vincristine are well known anticancer drugs: their action of disrupting mitotic spindle microtubules preferentially inhibits hyperproliferative cells. The third group consists of agents, including taxol, which promotes the polymerization of tubulin and thus stabilizes microtubules.

However, merely having activity as an antimitotic poison does not guarantee efficacy against a tumor cell, and certainly not a tumor cell which exhibits a drug-resistant phenotype. Vinca alkaloids such as vinblastine and vincristine are effective against neoplastic cells and tumors, yet they lack activity against some drug-resistant tumors and cells. One basis for a neoplastic cell displaying drug resistance (DR) or multiple-drug resistance (MDR) is through the over-expression of P-glycoprotein. Compounds which are poor substrates for transport of P-glycoprotein should be useful in circumventing such a MDR phenotype.

Accordingly, the exhibition of the DR or MDR phenotype by many tumor cells and the clinically proven mode of action of anti-microtubule agents against neoplastic cells necessitates the development of anti-microtubule agents cytotoxic to non-drug resistant neoplastic cells as well as cytotoxic to neoplastic cells with a drug resistant phenotype.

BACKGROUND ART

Selected cryptophycin compounds, dioxa-diazacyclohexadecenetetrones isolated or synthesized from isolates from the blue-green algae (cyanobacteria) of the genus Nostoc, were characterized as antifungal agents with activity toward filamentous fungi, specifically the Aspergillus, Penicillium and Phoma species thereof; however, their mechanism of action was unknown. Five cryptophycin compounds, herein designated Cryptophycins 1, 3, 5, 13 and 15, were disclosed in U.S. Pat. Nos. 4,946,835, 4,845,085, 4,845,086, and 4,868,208, such compounds either having been isolated from a strain of Nostoc sp. designated MB 5357 or having been synthesized from such an isolated compound.

SUMMARY OF THE INVENTION

The present invention provides novel cryptophycin compounds having the following structure:

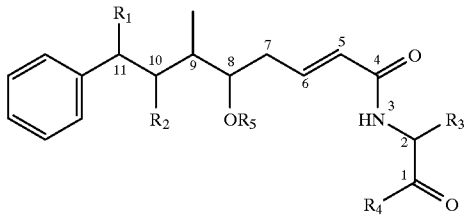

Wherein $R_1$ is H, OH, a halogen, O of a ketone group, $NH_2$, SH, a lower alkoxyl group or a lower alkyl group;

$R_2$ is H, OH, O of a ketone group, $NH_2$, SH, a lower alkoxyl group or a lower alkyl group; or $R_1$ and $R_2$ may be taken together to form an epoxide ring, an aziridine ring, a sulfide ring or a second bond between $C_{10}$ and $C_{11}$;

$R_3$ is a benzyl, hydroxybenzyl, methoxybenzyl, halohydroxybenzyl or halomethoxybenzyl group;

$R_4$ is OH, a lower β-amino acid wherein $C_1$ is bonded to N of the β-amino acid, or an esterified lower β-amino acid wherein $C_1$ is bonded to N of the esterified lower β-amino acid group; and $R_5$ is H, a lower alkanoyl group or a lower a-hydroxy alkanoyl group; or $R_4$ and $R_5$ may be taken together to form a didepsipeptide group consisting of a lower β-amino acid bonded to a lower α-hydroxy alkanoic acid;

with the following provisos:

$R_1$ is H, a lower alkyl group, or a lower alkoxyl group only if $R_2$ is OH, O of a ketone group, $NH_2$, or SH;

$R_2$ is H, a lower alkyl group, or a lower alkoxyl group only if $R_1$ is OH, O of a ketone group, $NH_2$, or SH;

when $R_1$ is OH, $R_2$ is OH, and $R_4$ and $R_5$ are taken together to form the didepsipeptide with the following structure X:

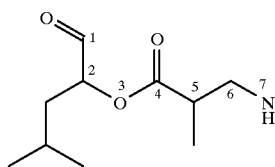

wherein $C_1$ of X corresponds to $R_5$ and $N_7$ corresponds to $R_4$, $R_3$ is not 3-chloro-4-methoxybenzyl;

when $R_1$ and $R_2$ are taken together to form an epoxide ring and $R_4$ and $R_5$ are taken together to form a didepsipeptide with the structure X, $R_3$ is not 3chloro-4-methoxybenzyl;

when $R_1$ and $R_2$ are taken together to form a second bond between $C_{10}$ and $C_{11}$ and $R_4$ and $R_5$ are taken together to form a didepsipeptide with the structure X, $R_3$ is not 3-chloro-4-methoxybenzyl; and when $R_1$ and $R_2$ are taken together to form an epoxide group, $R_4$ is bonded to N of either 3-amino-2-methylpropionic acid or 3-amino-2-methyl-propionic acid methyl ester, and $R_5$ is leucic acid, $R_3$ is not 3-chloro-4-methoxybenzyl.

Further provided by the present invention are methods for producing both novel and previously-disclosed cryptophycin compounds from the Nostoc sp. of blue-green algae (cyanobacteria). Pharmaceutical compositions comprising the new cryptophycin compounds are also provided by the present invention, as are methods for using both novel and previously-disclosed cryptophycin compounds to inhibit the proliferation of normal and hyperproliferative mammalian cells. The present invention also provides methods for using both novel and previously disclosed cryptophycin compounds to inhibit the proliferation of hyperproliferative mammalian cells with drug-resistant phenotypes, including those with multiple drug-resistant phenotypes. Furthermore, methods of using both novel and previously-disclosed cryptophycin compounds to treat pathological conditions, such as neoplasia, are provided by the present invention.

BRIEF DESCRIPTION OF THE FIGURES

FIG. 2A,B graphically present the effects of cryptophycin compounds and vinblastine on Jurkat cell proliferation and cell cycle progression. Jurkat cells were incubated with the indicated concentrations of cryptophycin compounds (A) or vinblastine (B) for 24 hours. For each sample, the number of viable cells (■) and the mitotic index (□) were determined as described in the Experimental section. Values represent the means±standard deviation (sd) for triplicate samples in one of three similar experiments.

DETAILED DESCRIPTION OF THE INVENTION

Figure 1:
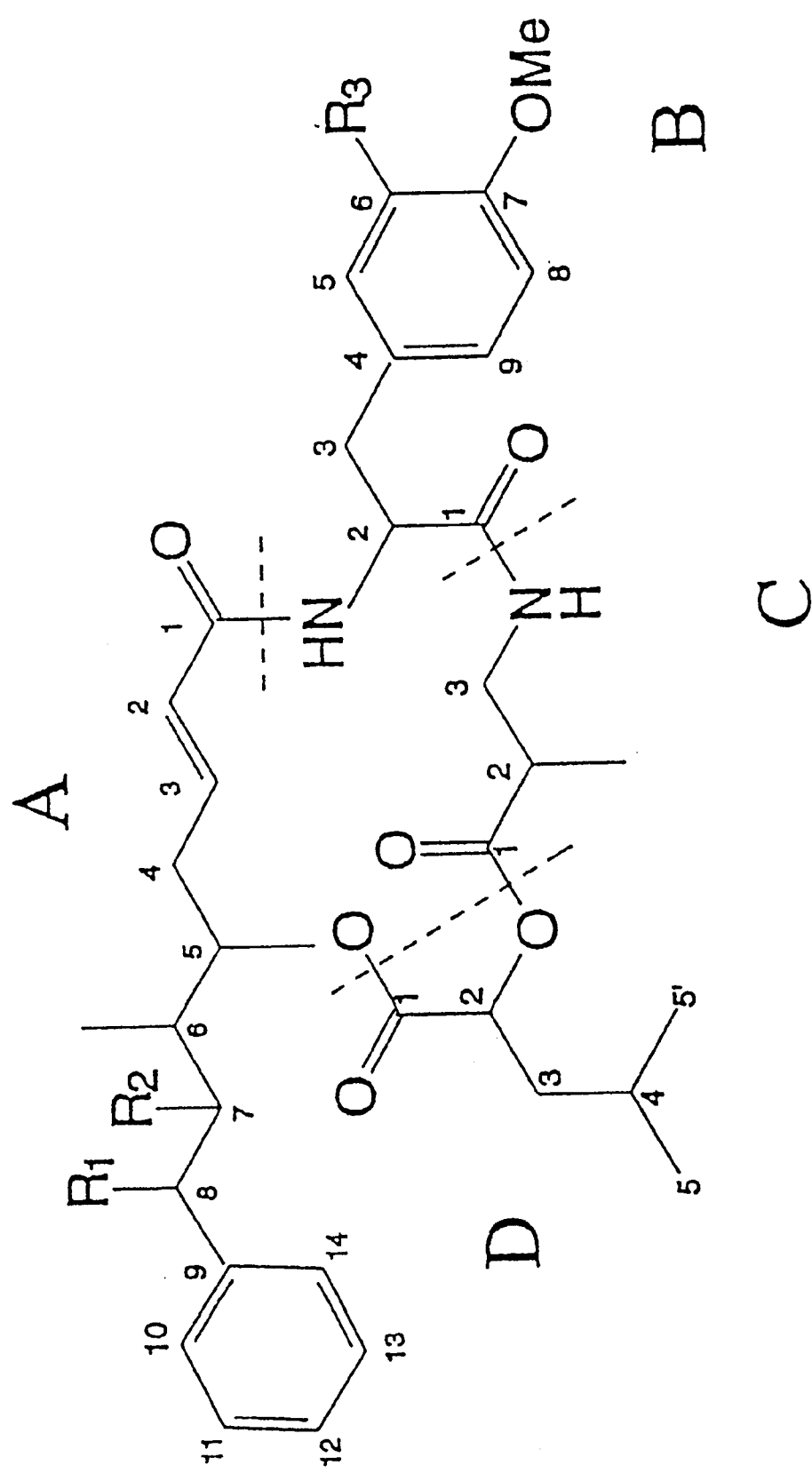
FIG. 1 provides a general structure of selected cryptophycin compounds of the present invention and a numbering system for the hydroxy acid units A and D and two amino acid units B and C in the selected embodiments.

The present invention provides novel cryptophycin compounds having the following structure:

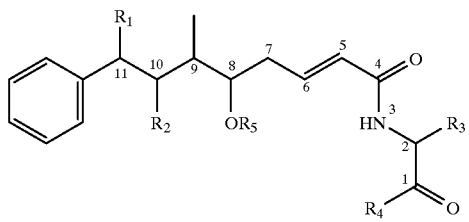

Wherein $R_1$ is H, OH, a halogen, O of a ketone group, $NH_2$, SH, a lower alkoxyl group or a lower alkyl group;

$R_2$ is H, OH, O of a ketone group, $NH_2$, SH, a lower alkoxyl group or a lower alkyl group; or $R_1$ and $R_2$ may be taken together to form an epoxide ring, an aziridine ring, a sulfide ring or a second bond between $C_{10}$ and $C_{11}$;

$R_3$ is a benzyl, hydroxybenzyl, methoxybenzyl, halohydroxybenzyl or halomethoxybenzyl group;

$R_4$ is OH, a lower β-amino acid wherein $C_1$ is bonded to N of the β-amino acid, or an esterified lower β-amino acid wherein $C_1$ is bonded to N of the esterified lower β-amino acid group; and $R_5$ is H, a lower alkanoyl group or a lower α-hydroxy alkanoyl group; or $R_4$ and $R_5$ may be taken together to form a didepsipeptide group consisting of a lower β-amino acid bonded to a lower α-hydroxy alkanoic acid;

with the following provisos:

$R_1$ is H, a lower alkyl group, or a lower alkoxyl group only if $R_2$ is OH, O of a ketone group, $NH_2$, or SH;

$R_2$ is H, a lower alkyl group, or a lower alkoxyl group only if $R_1$ is OH, O of a ketone group, $NH_2$, or SH;

when $R_1$ is OH, $R_2$ is OH, and $R_4$ and $R_5$ are taken together to form the didepsipeptide with the following structure X:

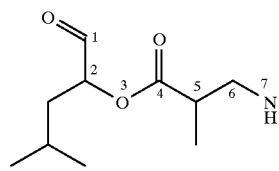

wherein $C_1$ of X corresponds to $R_5$ and $N_7$ corresponds to $R_4$, $R_3$ is not 3-chloro-4-methoxybenzyl;

when $R_1$ and $R_2$ are taken together to form an epoxide ring and $R_4$ and $R_5$ are taken together to form a didepsipeptide with the structure X, $R_3$ is not 3-chloro-4-methoxybenzyl;

when $R_1$ and $R_2$ are taken together to form a second bond between $C_{10}$ and $C_{11}$ and $R_4$ and $R_5$ are taken together to form a didepsipeptide with the structure X, $R_3$ is not 3-chloro-4-methoxybenzyl; and when $R_1$ and $R_2$ are taken together to form an epoxide group, $R_4$ is bonded to N of either 3-amino-2-methylpropionic acid or 3-amino-2-methyl-propionic acid methyl ester, and $R_5$ is leucic acid, $R_3$ is not 3-chloro-4-methoxybenzyl.

The invention further provides cryptophycin compounds wherein at least one of the groups attached to $C_2$, $C_8$, $C_9$, $C_{10}$, and $C_{11}$ have R stereochemistry. In a further embodiment of the invention, at least one of the groups attached to $C_2$, $C_8$, $C_9$, $C_{10}$, and $C_{11}$ have S stereochemistry.

The invention further provides cryptophycin compounds in accordance with the above structure where the structure of the didepsipeptide that is formed when $R_4$ is taken together with $R_5$ is the following structure X:

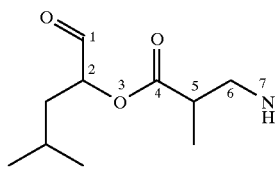

wherein $C_1$ of X corresponds to $R_5$ and $N_7$ of X corresponds to $R_4$.

As used herein, "lower β-amino acid" means any β-amino acid having three to eight carbons and includes linear and non-linear hydrocarbon chains; for example, 3-amino-2-methylpropionic acid. As used herein, "esterified lower β-amino acid" means any β-amino acid having three to five carbons where the hydrogen of the carboxylic acid group is substituted with a methyl group; for example, 3-amino-2methylpropionic acid methyl ester. As used herein, "lower alkanoyl group" means an alkanoyl group of one to seven carbons and includes linear and non-linear hydrocarbon chains. As used herein, "lower α hydroxyalkanoyl group" means an ahydroxyalkanoyl group of two to seven carbons and includes linear and non-linear hydrocarbon chains; for example, 2-hydroxy-4-methylvaleric acid.

As used herein, "lower alkoxyl group" means an alkyl group of one to five carbons in length bonded to an oxygen atom. As used herein, "lower alkyl group" means an alkyl group of one to five carbons and includes linear and non-linear hydrocarbon chains.

As used herein, "epoxide ring" means a three-member ring whose backbone consists of two carbons and an oxygen atom. As used herein, "aziridine ring" means a three-member ring whose backbone consists of two carbons and a nitrogen atom. As used herein, "sulfide ring" means a three-member ring whose backbone consists of two carbons and a sulfur atom.

As used herein, "halogen" refers to those members of the group on the periodic table historically known as the halogens. Methods of halogenation include, but are not limited to, the addition of hydrogen halides, substitution at high temperatures, photohalogenation, etc., and such methods are known to those of ordinary skill in the art.[1,2]

An example of a novel cryptophycin compound of the present invention is when $R_1$ and $R_2$ are taken together to form an epoxide group, $R_3$ is 4-methoxybenzyl, and $R_4$ and $R_5$ are taken together to form a didepsipeptide with the structure X. The structure of this cryptophycin compound, Cryptophycin 2, is the following:

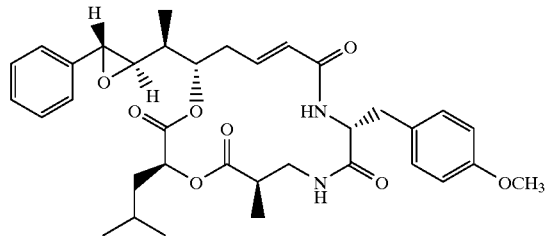

A further example of a novel cryptophycin compound of the present invention is when $R_1$ and $R_2$ are taken together to form a second bond between the $C_{10}$ and $C_{11}$ carbons such that there is a double bond, $R_3$ is 4-methoxybenzyl and $R_4$ and $R_5$ are taken together to form the didepsipeptide with the structure X. The structure of this cryptophycin compound, Cryptophycin 4, is the following:

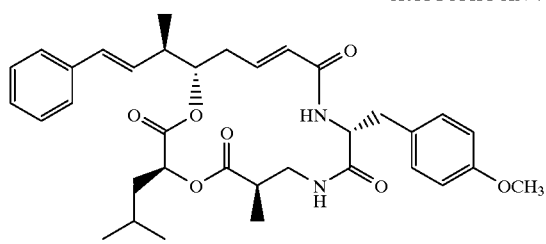

A further example of a novel cryptophycin compound of the present invention is when $R_1$ and $R_2$ are an OH group, $R_3$ is 3-chloro-4-methoxybenzyl, $R_4$ is 3-amino-2-methylpropionic acid methyl ester, and $R_5$ is hydrogen. The structure of this cryptophycin compound, Cryptophycin 6, is the following:

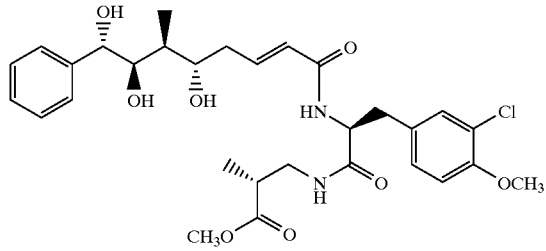

A further example of a novel cryptophycin compound of the present invention is when $R_1$, $R_2$, and $R_4$ are OH groups, $R_3$ is 3-chloro-4-methoxybenzyl, and $R_5$ is hydrogen. The structure of this cryptophycin compound, Cryptophycin 7, is the following:

CRYPTOPHYCIN 7

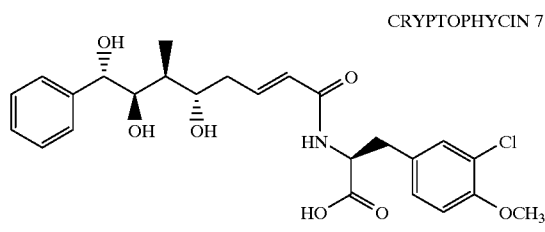

A further example of a novel cryptophycin compound of the present invention is when $R_1$ is a Cl group, $R_2$ is an OH group, $R_3$ is 3-chloro-4-methoxybenzyl, and $R_4$ and $R_5$ are taken together to form the didepsipeptide with the structure X. The structure of this cryptophycin compound, Cryptophycin 8, is the following:

CRYPTOPHYCIN 8

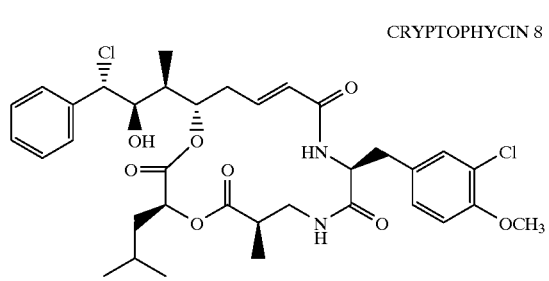

A further example of a novel cryptophycin compound of the present invention is when $R_1$ is an $OCH_3$ group, $R_2$ is an OH group, $R_3$ is 3-chloro-4-methoxybenzyl, and $R_4$ and $R_5$ are taken together to form the didepsipeptide with structure X. The structure of this cryptophycin compound, Cryptophycin 9, is the following:

CRYPTOPHYCIN 9

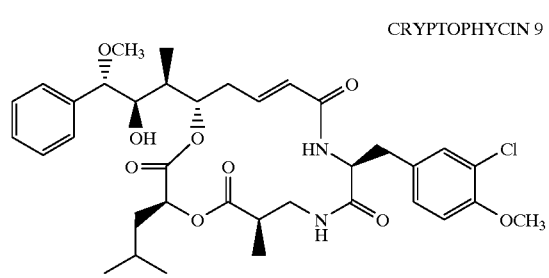

A further example of a novel cryptophycin compound of the present invention is when $R_1$ is a $OCH_3$ group, $R_2$ is a OH group, $R_3$ is 3-chloro-4-methoxybenzyl, $R_4$ is 3-amino-2-methyl-propionic acid and $R_5$ is hydrogen. The structure of this cryptophycin compound, Cryptophycin 10, is the following:

CRYPTOPHYCIN 10

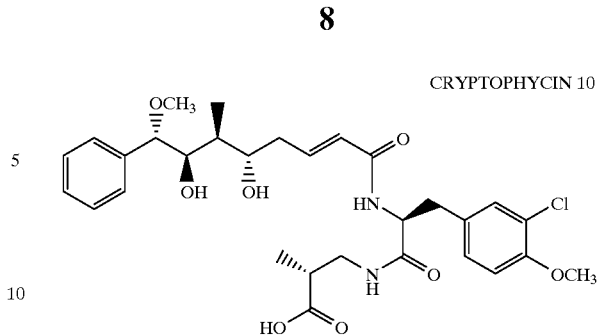

A further example of a novel cryptophycin compound of the present invention is when $R_1$ and $R_2$ are OH groups, $R_3$ is 3-chloro-4-methoxybenzyl, $R_4$ is 3-amino-2-methyl-propionic acid and $R_5$ is hydrogen. The structure of this cryptophycin compound, Cryptophycin 12, is the following:

CRYPTOPHYCIN 12

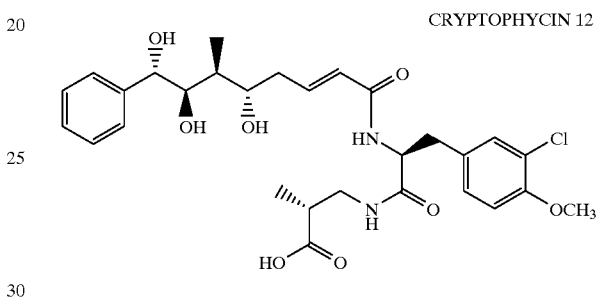

A further example of a novel cryptophycin compound of the present invention is when $R_1$ and $R_2$ are taken together to form a second bond between the $C_{10}$ and $C_{11}$ carbons to form a double bond $R_3$ is 3-chloro-4-methoxybenzyl, $R_4$ is 3-amino-2-methyl-propionic acid, and $R_5$ is hydrogen. The structure of this cryptophycin compound, Cryptophycin 14, is the following:

CRYPTOPHYCIN 14

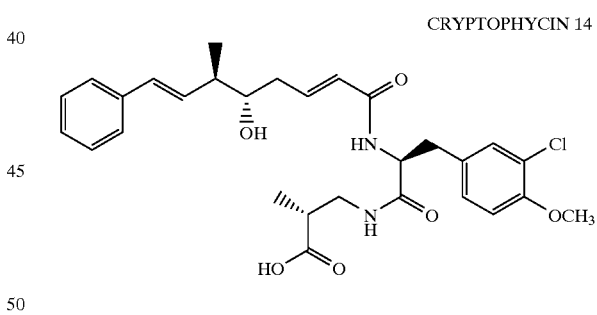

Of the above compounds, Cryptophycins 2, 4, 6 and 7 are metabolites produced by a strain of Nostoc sp. of blue-green algae (cyanobacteria) which has been cultured, with these compounds subsequently isolated from this culture. Cryptophycins 8, 9, 10–12 and 14 are derivatives of these naturally-produced metabolites, having been chemically modified with the methods described in the Experimental section of this application, with alternate methods to create the exemplified compounds, as well as the non-exemplified compounds, available to those of ordinary skill in the art.

The present invention provides methods of producing the above cryptophycin compounds through the culturing of a strain of the Nostoc sp. The morphological characteristics of the Nostoc sp. of blue-green algae (cyanobacteria), as provided in U.S. Pat. No. 4,946,835, are that they are filamentous and consist of vegetative cells. In longer filaments, heterocysts occasionally are observed in an intercalary position. Akinetes are not observed. Reproduction is by hormogonia in addition to random trichome breakage. The basis for an identification of a Nostoc sp. can be found in *J. Gen. Micro.*, 111:1–61 (1979).

The invention further provides that a Nostoc sp. may be cultured and that novel cryptophycin metabolites, as well as previously disclosed cryptophycin metabolites, may be isolated from this culture. In a preferred embodiment of the present invention, the Nostoc sp. strain designated GSV 224 is the strain which is cultivated and from which are isolated compounds represented by the following structure:

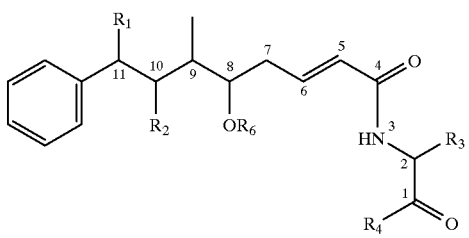

Wherein $R_1$ is H, OH, a halogen, O of a ketone group, $NH_2$, SH, a lower alkoxyl group or a lower alkyl group;

$R_2$ is H, OH, O of a ketone group, $NH_2$, SH, a lower alkoxyl group or a lower alkyl group; or $R_1$ and $R_2$ may be taken together to form an epoxide ring, an aziridine ring, a sulfide ring or a second bond between $C_{10}$ and $C_{11}$;

$R_3$ is a benzyl, hydroxybenzyl, methoxybenzyl, halohydroxybenzyl or halomethoxybenzyl group;

$R_4$ is OH, a lower β-amino acid wherein $C_1$ is bonded to N of the β-amino acid, or an esterified lower β-amino acid wherein $C_1$ is bonded to N of the esterified lower β-amino acid group; and $R_5$ is H, a lower alkanoyl group or a lower α-hydroxy alkanoyl group; or $R_4$ and $R_5$ may be taken together to form a didepsipeptide group consisting of a lower β-amino acid bonded to a lower α-hydroxy alkanoic acid;

with the following provisos:

$R_1$ is H, a lower alkyl group, or a lower alkoxyl group only if $R_2$ is OH, O of a ketone group, $NH_2$, or SH.

In a preferred embodiment of the invention, chemically modifying a cryptophycin metabolite isolated by the above method provides a distinct compound also having this structure. Procedures for chemically modifying cryptophycin compounds to produce additional compounds within the scope of the present invention are available to those of ordinary skill in the art. Moreover, additional procedures are described in greater detail in the Experimental section of this application.

In addition to the novel cryptophycin compounds of the present invention, the present invention provides novel methods of producing, as well as using, the above structure which includes the following previously disclosed cryptophycin species, Cryptophycins 1, 3, 5, 13 and 15. The structures of these compounds are the following:

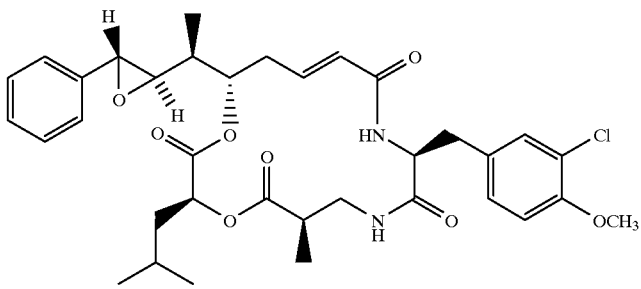

CRYPTOPHYCIN 1

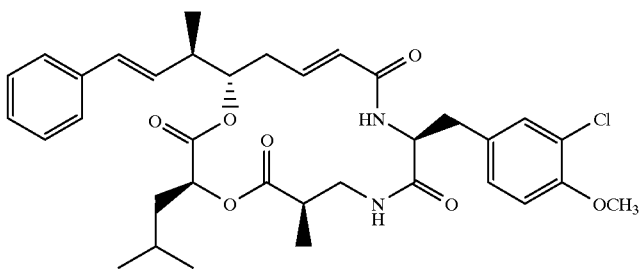

CRYPTOPHYCIN 3

-continued

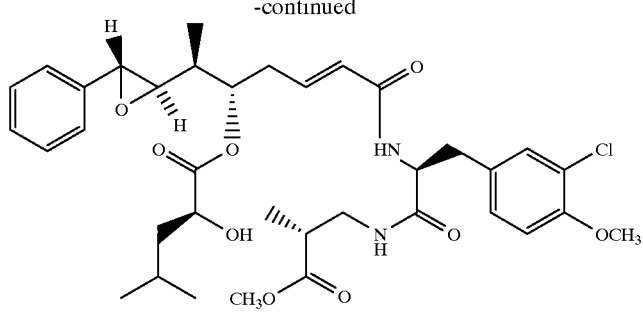

CRYPTOPHYCIN 5

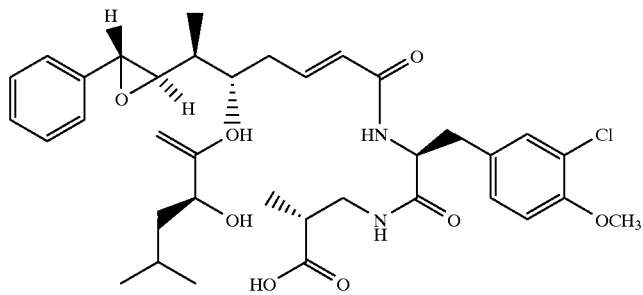

CRYPTOPHYCIN 13

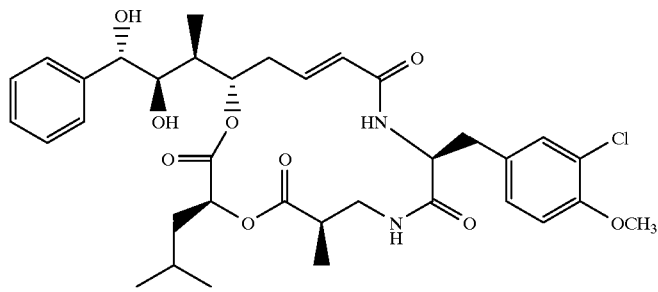

CRYPTOPHYCIN 15

The invention provided herewith is directed to any strain of the Nostoc sp. and preferably to the Nostoc sp. GSV 224 strain to produce cryptophycin compounds. To that end, the GSV 224 strain of Nostoc sp. was deposited on Oct. 7, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 55483. Other strains of Nostoc sp., in particular strain MB 5357 previously deposited by Merck and Co. under ATCC accession No. 53789, are strains contemplated to be utilized to practice the present invention.

As is the case with other organisms, the characteristics of Nostoc sp. are subject to variation. For example, recombinants, variants, or mutants of the specified strains may be obtained by treatment with various known physical and chemical mutagens, such as ultraviolet ray, X-rays, gamma rays, and N-methyl-N'-nitro-N-nitrosoguanidine. All natural and induced variants, mutants, and recombinants of the specified strains which retain the characteristic of producing a cryptophycin compound are intended to be within the scope of the claimed invention.

The cryptophycin compounds of the present invention can be prepared by culturing a strain of Nostoc sp. under submerged aerobic conditions in a suitable culture medium until substantial antibiotic activity is produced. Other culture techniques, such as surface growth on solidified media, can also be used to produce these compounds. The culture medium used to grow the specified strains can include any of one of many nitrogen and carbon sources and inorganic salts that are known to those of ordinary skill in the art. Economy in production, optimal yields, and ease of product isolation are factors to consider when choosing the carbon sources and nitrogen sources to be used. Among the nutrient inorganic salts which can be incorporated in the culture media are the customary soluble salts capable of yielding iron, potassium, sodium, magnesium, calcium, ammonium, chloride, carbonate, phosphate, sulfate, nitrate, and like ions.

Essential trace elements which are necessary for the growth and development of the organisms should also be included in the culture medium. Such trace elements commonly occur as impurities in other constituents of the medium in amounts sufficient to meet the growth requirements of the organisms. It may be desirable to add small amounts (i.e. 0.2 mL/L) of an antifoam agent such as polypropylene glycol (M.W. about 2000) to large scale cultivation media if foaming becomes a problem.

For production of substantial quantities of the cryptophycin compounds, submerged aerobic cultivation in tanks can be used. Small quantities may be obtained by shake-flask culture. Because of the time lag in metabolite production commonly associated with inoculation of large tanks with the organisms, it is preferable to use a vegetative inoculum. The vegetative inoculum is prepared by inoculating a small volume of culture medium with fragments of the vegetative trichome or heterocyst-containing form of the organism to obtain a fresh, actively growing culture of the organism. The vegetative inoculum is then transferred to a larger tank. The medium used for the vegetative inoculum can be the same as that used for larger cultivations or fermentation, but other media can also be used.

The organisms may be grown at temperatures between about 20° C. and 30° C. and an incident illumination intensity of about 100 to 200 $\mu$mol photons $m^{-2}sec^{-1}$ (photosynthetically active radiation).

As is customary in aerobic submerged culture processes of this type, carbon dioxide gas is introduced into the culture by addition to the sterile air stream bubbled through the culture medium. For efficient production of the cryptophycin compounds, the proportion of carbon dioxide should be about 1% (at 24° C. and one atmosphere of pressure).

The prior art, specifically U.S. Pat. No. 4,946,835, provides methods of cultivating Nostoc sp., the contents of which are hereby incorporated by reference.

Cryptophycin compound production can be followed during the cultivation by testing samples of the broth against organisms known to be sensitive to these antibiotics. One useful assay organism is *Candida albicans*.

Following their production under submerged aerobic culture conditions, cryptophycin compounds of the invention can be recovered from the culture and from the culture media by methods known to those of ordinary skill in this art. Recovery is generally accomplished by initially filtering the culture medium to separate the algal cells and then freeze-drying the separated cells. The freeze-dried alga can be extracted with a suitable solvent such as ethanol, methanol, isopropanol, or dichloromethane. The cryptophycins can be separated by subjecting this extract, as well as the culture media, to rapid chromatography on reversed-phase column. The cryptophycins can be purified by reversed-phase high-performance liquid chromatography (HPLC).

As will be apparent from their structures, the cryptophycin compounds have groups which are capable of chemical modification. The genus compound of the present invention contemplates those cryptophycins which exhibit anti-neoplastic activity. For example, the derivatives exemplified in the present invention include compounds having the epoxide oxygen or hydroxy groups on C-7 and C-8 of unit A or the leucic acid group of unit B of FIG. 1. Such derivatives of the novel and previously disclosed compounds which display the desired anti-neoplastic activity are included in the claimed invention. Moreover, the relationship between the structure of the cryptophycin compounds and anti-neoplastic activity is provided in the Experimental section hereinbelow.

While selected cryptophycin compounds are known to be metabolites produced by the alga of the present invention, other cryptophycin compounds, e.g. Cryptophycins 8–15, can be derived from the metabolites using published techniques which are known to those of ordinary skill in the art; for example, the syntheses disclosed in U.S. Pat. Nos. 4,868,208, 4,845,086, and 4,845,085, the contents of which are hereby incorporated by reference, or by utilizing other methods which are known to those of ordinary skill in the art. Moreover, the present invention provides methods of producing derivatives in the Experimental section.

The novel cryptophycin compounds of the present invention and the previously disclosed cryptophycin compounds can be therapeutically employed as antineoplastic agents and thereby used in methods to treat neoplastic diseases. As used herein, "neoplastic" pertains to a neoplasm, which is an abnormal growth, such growth occurring because of a proliferation of cells not subject to the usual limitations of growth. As used herein, "anti-neoplastic agent" is any compound, composition, admixture, co-mixture or blend which inhibits, eliminates, retards or reverses the neoplastic phenotype of a cell.

Chemotherapy, surgery, radiation therapy, therapy with biologic response modifiers, and immunotherapy are currently used in the treatment of cancer. Each mode of therapy has specific indications which are known to those of ordinary skill in the art, and one or all may be employed in an attempt to achieve total destruction of neoplastic cells. Chemotherapy utilizing one or more cryptophycins is provided by the present invention. Moreover, combination chemotherapy, chemotherapy utilizing cryptophycins in combination with other neoplastic agents, is also provided by the subject invention as combination therapy is generally more effective than the use of single anti-neoplastic agents. Thus, a further aspect of the present invention provides compositions containing a therapeutically effective amount of at least one new cryptophycin compound of the present invention, including nontoxic addition salts thereof, which serve to provide the above-recited therapeutic benefits. Such compositions can also be provided together with physiologically tolerable liquid, gel or solid carriers, diluents, adjuvants and excipients. Such carriers, diluents, adjuvants and excipients may be found in the *United States Pharmacopeia Vol. XXII and National Formulary Vol XVII*, U.S. Pharmacopeia Convention, Inc., Rockville, Md. (1989), the contents of which are herein incorporated by reference. Additional modes of treatment are provided in *AHFS Drug Information*, 1993 ed. by the American Hospital Formulary Service, pp. 522–660, the contents of which are herein incorporated by reference.

The present invention further provides that the pharmaceutical composition used to treat neoplastic disease contains cryptophycin compound and at least one additional anti-neoplastic agent. Anti-neoplastic compounds which may be utilized in combination with cryptophycin include those provided in *The Merck Index*, 11th ed. Merck & Co., Inc. (1989) pp. Ther 16–17, the contents of which are hereby incorporated by reference. In a further embodiment of the invention, anti-neoplastic agents may be antimetabolites which may include, but are not limited to, methotrexate, 5-fluorouracil, 6-mercaptopurine, cytosine arabinoside, hydroxyurea, and 2-chlorodeoxyadenosine. In another embodiment of the present invention, the anti-neoplastic agents contemplated are alkylating agents which may include, but are not limited to, cyclophosphamide, melphalan, busulfan, paraplatin, chlorambucil, and nitrogen mustard. In a further embodiment of the subject invention, the antineoplastic agents are plant alkaloids which may include, but are not limited to, vincristine, vinblastine, taxol, and etoposide. In a further embodiment of the present invention, the anti-neoplastic agents contemplated are antibiotics which may include, but are not limited to, doxorubicin (adriamycin), daunorubicin, mitomycin c, and bleomycin. In a further embodiment of the subject invention, the anti-neoplastic agents contemplated are hormones which may include, but are not limited to, calusterone, diomostavolone, propionate, epitiostanol, mepitiostane, testolactone, tamoxifen, polyestradiol phosphate, megesterol acetate, flutamide, nilutamide, and trilotane. In a further embodiment of the subject invention, the anti-neoplastic agents contemplated include enzymes which may include, but are not limited to, L-Asparaginase or aminoacridine derivatives which may include, but are not limited to, amsacrine. Additional anti-neoplastic agents include those provided in Skeel, Roland T., "Antineoplastic Drugs and Biologic Response Modifier: Classification, Use and Toxicity of Clinically Useful Agents," *Handbook of Cancer Chemotherapy* (3rd ed.), Little Brown & Co. (1991), the contents of which are herein incorporated by reference.

These compounds and compositions can be administered to mammals for veterinary use, such as for domestic animals, and clinical use in humans in a manner similar to other therapeutic agents. In general, the dosage required for therapeutic efficacy will vary according to the type of use and mode of administration, as well as the particularized requirements of individual hosts. Ordinarily, dosages will range from about 0.001 to 1000 $\mu$g/kg, more usually 0.01 to 10 $\mu$g/kg, of the host body weight. Alternatively, dosages within these ranges can be administered by constant infusion over an extended period of time, usually exceeding 24 hours, until the desired therapeutic benefits have been obtained. Indeed, drug dosage, as well as route of administration, must be selected on the basis of relative effectiveness, relative toxicity, growth characteristics of tumor and effect of cryptophycins on cell cycle, drug pharmacokinetics, age, sex, physical condition of the patient, and prior treatment.

The cryptophycin compounds, with or without additional anti-neoplastic agents, may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Such salts may also be formed as acid addition salts with any free cationic groups and will generally be formed with inorganic acids such as, for example, hydrochloric or phosphoric acids, or organic acids such as acetic, oxalic, tartaric, mandelic, and the like. Additional excipients which the further invention provides are those available to one of ordinary skill in the art, for example, that found in the *United States Pharmacopeia Vol. XXII and National Formulary Vol XVII*, U.S. Pharmacopeia Convention, Inc., Rockville, Md. (1989), which is herein incorporated by reference.

The suitability of particular carriers for inclusion in a given therapeutic composition depends on the preferred route of administration. For example, antineoplastic compositions may be formulated for oral administration. Such compositions are typically prepared either as liquid solution or suspensions, or in solid forms. Oral formulations usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

Compositions of the present invention may also be prepared as injectable, either as liquid solutions, suspensions, or emulsions; solid forms suitable for solution in, or suspension in, liquid prior to injection may be prepared. Such injectables may be administered subcutaneously, intravenously, intraperitoneally, intramuscularly, intrathecally, or intrapleurally. The active ingredient or ingredients are often mixed with diluents or excipients which are physiologically tolerable and compatible with the active ingredient(s). Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents.

The invention further provides methods for using cryptophycin compounds encompassed by the genus structure to inhibit the proliferation of mammalian cells by contacting these cells with a cryptophycin compound in an amount sufficient to inhibit the proliferation of the mammalian cell. A preferred embodiment is a method to inhibit the proliferation of hyperproliferative mammalian cells. For purposes of this invention, "hyperproliferative mammalian cells" are mammalian cells which are not subject to the characteristic limitations of growth, e.g., programmed cell death (apoptosis). A further preferred embodiment is when the mammalian cell is human. The invention further provides contacting the mammalian cell with at least one cryptophycin compound and at least one additional anti-neoplastic agent. The types of anti-neoplastic agents contemplated are the same as those disclosed hereinabove.

The invention further provides methods for using cryptophycin compounds encompassed by the genus structure to inhibit the proliferation of hyperproliferative cells with drug-resistant phenotypes, including those with multiple drug-resistant phenotypes, by contacting said cell with a cryptophycin compound in an amount sufficient to inhibit the proliferation of a hyperproliferative mammalian cell. A preferred embodiment is when the mammalian cell is human. The invention further provides contacting the mammalian cell with a cryptophycin compound and at least one additional anti-neoplastic agent. The types of anti-neoplastic agents contemplated are the same as those disclosed hereinabove.

The invention further provides a method for alleviating pathological conditions caused by hyperproliferating mammalian cells, for example, neoplasia, by administering to a subject an effective amount of a pharmaceutical composition provided hereinabove to inhibit the proliferation of the hyperproliferating cells. As used herein "pathological condition" refers to any pathology arising from the proliferation of mammalian cells that are not subject to the normal limitations of cell growth. Such proliferation of cells may be due to neoplasms, including, but not limited to the following neoplasms: mammary, small-cell lung, non-small-cell lung, colorectal, leukemia, melanoma, central nervous system (CNS), ovarian, prostate, sarcoma of soft tissue or bone, head and neck, gastric which includes pancreatic and esophageal, stomach, myeloma, bladder, renal, neuroendocrine which includes thyroid and lymphoma, non-Hodgkin's and Hodgkin's. In a further embodiment of the invention, the neoplastic cells are human. The present invention further provides methods of alleviating such pathological conditions utilizing cryptophycin in combination with other therapies, as well as other anti-neoplastic agents. Such therapies and their appropriateness for different neoplasia may be found in *Cancer Principles and Practice of Oncology*, 4th ed., Editors DeVita, V., Hellman, S., and Rosenberg., S., Lippincott Co. (1993), the contents of which are herein incorporated by reference.

In the present disclosure, cryptophycin compounds are shown to potently disrupt the microtubule structure in cultured cells. In addition, and in contrast with the Vinca alkaloids, cryptophycin compounds appear to be a poor substrate for the drug-efflux pump P-glycoprotein. Cryptophycin 1 is the major cytotoxin in the blue-green alga (cyanobacteria) Nostoc sp. strain designated GSV 224 and shows excellent activity against tumors implanted in mice.

This cyclic didepsipeptide had previously been isolated from Nostoc sp. ATCC accession no. 53787 as an antifungal agent and its gross structure was previously determined. The relative and absolute stereochemistry of this potentially important drug has now been established using a combination of chemical and spectral techniques. Six additional cryptophycin compounds, Cryptophycins 2–7 have also been isolated from GSV 224 and their total structures and cytotoxicities determined. Two types of cryptophycin compounds are present in this alga, one possessing a monochlorinated L-O-methyltyrosine unit and one possessing a non-chlorinated D-O-methyltyrosine unit. Several derivatives and degradation products are described, both chemically and pharmacologically.

The following examples serve to illustrate certain preferred embodiments and aspects of the present invention and are not to be construed as limiting the scope thereof.

Experimental

In the experimental disclosure which follows, all weights are given in grams (g), milligrams (mg), micrograms (μg), nanograms (ng), picograms (pg) or moles (mol), all concentrations are given as percent by volume (%), molar (M), millimolar (mM), micromolar (μM), nanomolar (nM), or picomolar (pM), normal (N) and all volumes are given in liters (L), milliliters (mL) or microliters (μL), and measures in millimeters (mm), unless otherwise indicated.

The following examples demonstrate the isolation and synthesis of cryptophycin compounds as well as their use as therapeutic agents in accordance with the invention.

In screening extracts of over 1000 blue-green algae (cyanobacteria) for antitumor activity, the lipophilic extract of Nostoc sp. GSV 224 was found to be strongly cytotoxic.[3] exhibiting minimum inhibitory concentrations (MICs) of 0.24 ng/mL against KB, a human nasopharyngeal carcinoma cell line, and 6 ng/mL against LoVo, a human colorectal adenocarcinoma cell line. More importantly, this extract showed significant tumor selective cytotoxicity in the Corbett assay.[4, 5] Bioassay monitored reversed-phase chromatography of the algal extract led to a fraction which was predominantly Cryptophycin 1, a potent fungicide that had been isolated earlier from Nostoc sp. ATCC 53789 by researchers at Merck[6,7] and found to be very active against strains of Cryptococcus.

Cryptophycin 1 accounted for most of the cytotoxic activity of the crude algal extract of Nostoc sp. GSV 224 and the pure compound showed $IC_{50}$ values of 3 and 5 pg/mL against KB and LoVo, respectively. In the Corbett assay Cryptophycin 1 was found to be strongly tumor selective and equally cytotoxic against drug-sensitive and drug-resistant tumor cells. Immunofluorescence assays showed that Cryptophycin 1 interact with a cellular target similar to that of vinblastine, but differed from the latter drug in having a longer time course of action and in not forming paracrystalline bodies. In preliminary in vivo experiments, Cryptophycin 1 exhibited very promising activity against tumors implanted in mice.

Minor amounts of several other cryptophycin compounds were present in Nostoc sp. GSV 224 and six of these could be isolated in sufficient quantities by reversed-phase HPLC for structure determinations and antitumor evaluation in vitro. Cryptophycins 2, 3, 4, 5, and 6 accompanied Cryptophycin 1 in the fraction eluted from a reversed-phase flash column with 3:1 methanol/water. Cryptophycin 7 was found in an earlier, less cytotoxic fraction eluted with 1:3 methanol/water.

Cryptophycins 3 and 5 appeared to be identical with fungicidal semi-synthetic compounds prepared from Cryptophycin 1 by researchers at Merck.[8,9] Cryptophycin 3 was prepared by treating Cryptophycin 1 with a zinc-copper couple or with diphosphorus tetraiodide.[8] Cryptophycin 5 was prepared by methanolysis of Cryptophycin 1.[9]

EXAMPLE 1

Structure Determination

The determination of the structures of the new compounds, viz. Cryptophycins 2, 4, 6 and 7, 8, 9, 10, 12 and 14, as well as those previously disclosed, were carried out in a straightforward manner using methodology that is well-known to those trained in the art. Mass spectral data were consistent with the molecular compositions. Proton and carbon NMR data obtained from COSY, HMQC, HMBC and NOESY spectra allowed one to assemble all of the gross structures of these depsipeptide-type compounds. The presence of the various hydroxy and amino acid units in each compound were confirmed by gas chromatographic mass spectral analysis. Total structures, including absolute stereochemistries, were determined using a combination of chemical degradative and special analytical techniques on appropriate derivatives of the cryptophycin compounds.

EXAMPLE 2

Structure-Activity Relationships (SAR)

To probe the structural features in Cryptophycin 1 needed for optimal activity, derivatives were prepared for SAR studies.

Cryptophycins 8 and 9 were prepared to evaluate the need of the epoxide group in unit A of Cryptophycin 1 (see FIG. 1) for maximum activity. Cryptophycin 8 was prepared by treating Cryptophycin 1 with hydrochloric acid to form a chlorohydrin. Cryptophycin 9 was produced from Cryptophycin 1 by mild acid-catalyzed methanolysis.

To evaluate the need of the leucic acid unit in Cryptophycin 1 (unit D in FIG. 1) for maximum activity, Cryptophycins 6 and 7 were available for SAR studies. The leucic acid unit was easily removed by saponification. For example, mild saponification of (i) Cryptophycin 9 produced Cryptophycin 10, (ii) Cryptophycins 1, 5 and 8 produced Cryptophycin 12, and (iii) Cryptophycin 3 produced Cryptophycin 14.

Most of the compounds were first tested for cytotoxicity against KB and LoVo. KB and LoVo $IC_{50}$ values for Cryptophycin 1–10 and 12 are listed in Table 1. Cryptophycins 1 and 2 were consistently the most cytotoxic of the twelve compounds. The potent cytotoxicity of Cryptophycin 1 was retained even when the epoxide ring was opened by HCl to form a chlorohydrin and produce Cryptophycin 8, but was diminished a thousand-fold when the epoxide ring was opened by methanolysis to give Cryptophycin 9. Removal of the epoxide oxygen or hydroxy groups from C-7 and C-8 of unit A as found in Cryptophycins 3 and 4 resulted in a hundredfold decrease in cytotoxicity. From these results one could conclude that a group was needed on either C8 or C9 or on both C8 and C9 of unit A that could coordinate either a non-bonding pair of electrons on an oxygen or other electronegative element attached to C8/C9 of the π-electrons in the C8–C9 double bond to a receptor site in the drug target. Moreover, the results suggested that analogs possessing any combination of one or two hydroxy, keto, or amino groups attached to C8/C9 might be just as active as Cryptophycin 1; however, analogs possessing more bulky methoxy or methylamino groups on C8/C9 would probably have diminished activity.

The cytotoxicities of Cryptophycins 1 and 2 were found to be identical, strongly suggesting that the chloro substitute on the O -methyltyrosine and a certain absolute configuration for the B unit (see FIG. 1) are not needed for the potent cytotoxicity. Since activity appears to be independent of the absolute configuration of this unit, an O-methyltyrosine unit at this position may not be required for optimal cytotoxicity.

In fact, the lack of a difference in activity suggests that any D- or L-α-amino acid may be present in unit B without having any appreciable effect on the cytotoxicity. With respect to the general cryptophycin structure of the present invention, any group attached to the $C_2$ of an α-amino acid may be present without having an appreciable effect on the cytotoxicity.

Cryptophycin 5 displayed essentially the same cytotoxicity as Cryptophycins 1 and 2, indicating that the cyclized depsipeptide is unnecessary for full activity.

The leucic acid unit (unit D in FIG. 1), however, appears profoundly important for potent activity, since 6, 7, 10 and 12 are very weakly cytotoxic and 14 is a thousand-fold less cytotoxic than Cryptophycin 1. Analogs with a different, but similar a-hydroxyacid residue for unit D [e.g. 2-hydroxy-3-methylvaleric acid (isoleucic acid) would be expected to have essentially the same activity. One would also expect an analog with the corresponding a-amino acid for unit D (e.g. leucine in lieu of leucic acid) to have strong activity.

After testing the Cryptophycin compounds for cytotoxicity against KB and LoVo, the most active compounds were then evaluated for selective cytotoxicity against four different cell types, viz. a murine leukemia (L1210 or P388), a murine solid tumor (colon adenocarcinoma 38, pancreatic ductal adenocarcinoma 03, mammary adenocarcinoma M16/M17), a human solid tumor (colon CX-1, HCT8, H116; lung H125; mammary MX-1, MCF-7), and a low malignancy fibroblast (LML), using the Corbett assay,[2] a disk diffusion assay modeled after the one commonly used in antifungal and antibacterial testing. The results, shown in Table 1, indicated that Cryptophycins 1–5 and 8 were neither solid tumor nor leukemia selective, but rather equally active against tumor cell lines, including drug-resistant ones such as M17. None of the compounds showed a zone of inhibition for any of the solid tumor cell lines that was $\geq 250$ zone units, i.e. $\geq 7.5$ mm, larger than the zone of inhibition for the leukemia cell line. Cryptophycins 1–5 and 8, however, displayed markedly larger zones of inhibition ($\geq 400$ zone units) for all of the tumor cell lines compared with the zone of inhibition for the fibroblast LML. Diagnostically LML has been found to behave more like a normal cell than a tumor cell with respect to clinically-useful cytotoxic agents (see Corbett assay data for 5-fluorouracil, etoposide and taxol in Table 1). Since the differential cytotoxicities were >250 zone units, Cryptophycins 1–5 and 8 were tumor selective. These compounds therefore became candidates for in vivo testing.

To date only Cryptophycin 1 has been evaluated in vivo. It is active against the four tumors tested so far (Table 2) and exhibits excellent activity against two of them, viz. colon adenocarcinomas #38 and #51, showing tumor burden T/C (mean tumor burden in treated animals/mean tumor burden untreated animals) values that are less than 10%.[9] T/C values that are less than 42% are considered to be active by NCI standards; T/C values that are less than 10% are considered to have excellent activity by NCI standards. Lethal toxicity observed during testing was attributed to leucopenia which is common to all clinically used antitumor drugs.

TABLE 1

Cytotoxicity data for cryptophycins and semi-synthetic analogs.
Corbett/Valeriote assay data for 5-fluorouracil, etoposide (VP-16) and taxol are included for comparison.
Type of Cytotoxicity (Differential in Zone Units)

| Compound | μg/disk | Corbett Assay[a] | μg/disk | Valeriote Assay[b] | KB IC$_{50}$ ng/mL | Lo Vo IC$_{50}$ ng/mL |
|---|---|---|---|---|---|---|
| 1 | 12.5 | E/T(>400)[c] | | N | 0.005 | 0.003 |
| 2 | 25 | E/T(>400)[c] | | N | 0.007 | 0.0002 |
| 3 | 25 | E/T(>400)[c] | | N | 0.3 | 0.5 |
| 4 | 20 | E/T(>400)[c] | | N | 1.3 | 0.5 |
| 5 | 2.9 | E/T(>600)[c] | | N | 0.02 | 0.02 |
| 6 | 250 | I | | | $\geq 100$ | $\geq 100$ |
| 7 | | | | | $\geq 750$ | $\geq 480$ |
| 8 | 30 | E/T(>500)[c] | 30 | N | 0.0002 | 0.01 |
| 9 | | | | | 15 | Not Deterrmined |
| 10 | | | | | $\geq 100$ | $\geq 100$ |
| 12 | | | | | $\geq 100$ | $\geq 100$ |
| 14 | | | | | 1.8 | 3 |
| 5-FU | 2.5 | M/T(>400)[d] | 2.5 | LL(>400) | | |
| VP-16 | 5 | L(350), T(530)[d] | 5 | LL(260) | | |
| taxol | 0.2 | M/H/T($\geq 400$)[d] | | | | |

[a]L = leukemia selective (e.g. $Z_{L1210}-Z_{C38}$ and $Z_{L1210}-Z_{H8} \geq 250$ zu)
M = murine solid tumor selective (e.g. $Z_{C38}-Z_{L1210} \geq 250$ zu)
H = human solid selective (e.g. $Z_{H8}-Z_{L1210} \geq 250$ zu)
E = equally cytotoxic towards leukemia and solid tumor cell lines (inhibition zones $\geq 250$ zu)
T = tumor selective (e.g. $Z_{L1210}-Z_{LML}$, $Z_{C38}-Z_{LML}$, and $Z_{H8}-Z_{LML} \geq 250$ zu
I = inactive (inhibition zones < 250)
[b]N = non-selective towards tumor (leukemia) and normal cell (CFU-GM) lines
LL = lymphocytic leukemia selective ($Z_{L1210}-Z_{CFU-GM} \geq 250$ zu)
ML = acute myelogenous leukemia (AML) selective ($Z_{AML}-Z_{CFU-GM} \geq 250$ zu).
[c]Selective against drug-sensitive and drug-resistant cell lines ($Z_{C38}-Z_{LML}$, $Z_{M17}-Z_{LML}$ and $Z_{H8}-Z_{LML}$).
[d]Selective against drug-sensitive cell lines only.

EXAMPLE 3

Culture Conditions

Nostoc sp. GSV 224 was obtained from Professor C. P. Wolk, MSU-DOE Plant Research Laboratory, Michigan State University. Nostoc sp. ATCC 53789 was purchased from the American Type Culture Collection. A 1 L flask culture of alga was used to inoculate an autoclaved 20 L glass carboy containing an inorganic medium, designated modified BG-11,[3] the pH of which had been adjusted to 7.0 with NaOH. Cultures were continuously illuminated at an incident intensity of 200 $\mu$mol photons $M^{-2}$ $sec^{-1}$ (photosynthetically active radiation) from banks of cool-white fluorescent tubes and aerated at a rate of 5L/min with a mixture of 0.5% $CO_2$ in air at a temperature of 24±1° C. Typically, the culture was harvested by filtration after 21 days. The yields of lyophilized Nostoc sp. GSV 224 and ATCC 53789 averaged 0.61 and 0.3 g/L of culture, respectively.

EXAMPLE 4

Isolation

The lyophilized Nostoc sp. GSV 224 (12.23g) was extracted twice with 700 mL and 400 mL portions of MeOH for 12 and 5 hours (h), respectively. The extracts were combined and concentrated in vacuo to give 1.84 g of a dark green solid which was partitioned between water and $CH_2Cl_2$. The lipophilic portion (0.65 g; KB MIC 0.24 ng/mL) was applied to an ODS-coated silica column (55 g, 7×5 cm) and subjected to flash chromatography with 1:3 MeOH/$H_2O$ (0.8 L), 1:1 MeOH/$H_2O$ (0.8 L), 3:1 MeOH/$H_2O$ (0.8 L), MeOH (0.8 L), and $CH_2Cl_2$ (0.5 L). The fraction that was eluted with 3:1 MeOH/$H_2O$ (22 mg; KB MIC 14 pg/mL), which accounted for essentially all of the cytotoxic activity, was subjected to reversed-phase HPLC (Econosil C18, 10 $\mu$u, 250 cm×10 mm, UV detection at 250 nm, flow rate 3 mL/min) using 1:5 MeOH/$H_2O$ as the eluant to give Cryptophycins 7 (tR 7.6 min, 0.2 mg), 5 ($t_R$ 15.4 min, 2.3 mg), 2 ($t_R$ 16.0 min, 1.0 mg), 1 ($t_R$ 19.0 min, 12.0 mg), 4 ($t_R$ 26.5 min, 1.2 mg), and 3 ($t_R$ 30.2 min, 1.4 mg). From one of the cultures the fraction (8.1 mg) that eluted from the flash column with 1:3 MeOH/$H_2O$ showed milder cytotoxicity (KB MIC 2 $\mu$g/mL). Purification on HPLC using 2:3 MeOH/$H_2O$ as the eluant yielded cryptophycin G (7, $t_R$ 6.0 min, 2.4 mg).

EXAMPLE 5

Spectral Data for Cryptophycins 1–7

The bold italicized letters in the spectral data refer to the units A–D in FIG. 1.

Cryptophycin 1

$[\alpha]_D$+33.8°(MeOH, c 1.83); UV $\lambda_{max}(\beta)$ 208 (42,400), 218 (33,700), 228 (23,800), 280 (2,210); CD $[\theta]_{202}$+15,900, $[\theta]_{206}$+64,900, $[\theta]_{214}$+26,900, $[\theta]_{244}$+46,300, $[\theta]_{237}$+10,500. IR (CHCl$_3$) $\nu_{max}$ 3425, 2963, 1751, 1719, 1677, 1502, 1259 cm$^{-1}$. EIMS m/z (rel intensity) 654/656 (20/9), 412/414 (33/12), 280/282 (31/12), 227 (80), 195/197 (92/44), 91 (100); high resolution EIMS n/z 654.2665 (calcd for $C_{35}H_{43}ClN_2O_8$, 4.3 mmu error). $^1$H NMR (CDCl$_3$): amino or hydroxy acid unit δ (carbon position, multiplicity; J in Hz) 7,8-epoxy-5-hydroxy-6-methyl-8-phenyl-2-octenoic acid (A) 5.74 (2, dt; 15.5 and 0.9), 6.68 (3, ddd; 15.5, 9.6 and 5.2), 2.45 (4, ddd; 14.2, 11.1 and 9.6), 2.55 (4, brdd; 14.2 and 5.2), 5.16 (5, ddd; 11.1, 4.9 and 1.9), 1.80 (6, m), 1.14 (6-Me, d; 7.1), 2.92 (7, dd; 7.5 and 2.0), 3.69 (8d; 2.0), 7.25 (10/14, m), 7.34–7.39 (11/12/13, m); leucic acid (D) 4.83 (2, dd; 6.8 and 3.3), 1.70 (3, m), 1.36 (3, m), 1.70(4, m), 0.86 (5, d; 6.6), 0.85 (5', d;6.6); 3-amino-2-methylpropionic acid (C) 2.71 (2, m), 1.22 (2-Me, d; 7.1), 3.30 (3, ddd; 13.4, 5.8 and 3.8), 3.48 (3, ddd; 13.4, 6.3 and 5.8), 6.93 (3-NH, brt; 5.8); 3-chloro-4-methoxyphenylalanine (B) 4.80 (2, ddd; 8.7, 7.3 and 5.4), 5.61 (2-NH, d; 8.7), 3.03 (3, dd; 14.4 and 7.3), 3.13 (3, dd; 14.4 and 5.4), 7.21 (5, d; 2.1), 3.87 (7-OCH$_3$,s), 6.83 (8, d; 8.5), 7.07 (9, dd; 8.5 and 2.1). $^{13}$C NMR (CDCl$_3$): unit δ (carbon position) A 165.3 (1), 125.3 (2), 141.0 (3), 36.7 (4), 76.2 (5), 40.6 (6), 13.5 (6-Me), 63.0 (7), 59.0 (8), 136.7 (9), 125.6 (10/14), 128.7 (11/13), 128.5 (12), D 170.7 (1), 71.3 (2), 39.4 (3), 24.5 (4), 22.9 (5), 21.3 (5'); C 175.6(1), 38.2 (2), 14.1 (2-Me), 41.1 (3); B 170.9 (1), 53.6 (2), 35.0 (3), 129.7 (4), 131.0 (5), 122.4 (6), 154.0 (7), 56.1 (7-OCH$_3$), 112.2 (8), 128.4 (9).

Cryptophycin 2

$[\alpha]_D$+20.4°(MeOH, c 0.54); UV $\lambda_{max}(\epsilon)$ 206 (43,800), 218 (37,500), 232 (22,900), 278 (2,410); CD $[\theta]_{203}$+54,100, $[\theta]_{212}$+16,500, $[\theta]_{225}$+53,600, $[\theta]_{236}$–14,000. IR (CHCl$_3$) $\nu_{max}$ 3423, 3029, 2961, 1742, 1724, 1678, 1512, 1258 cm$^{-1}$. EIMS m/z (rel intensity, assignment) 620 (11, M$^+$), 431 (3), 378(8), 377 (6), 311 (11), 246 (10), 244 (8), 227 (14), 195 (17), 161 (84, CH$_3$O—C$_6$H$_4$—CH=CH=CO$^+$), 121 (79, CH$_3$O—C$_6$H$_4$—CH$_2^+$), 91 (100); high resolution EIMS m/z 620.3094 (calcd for $C_{35}H_{44}N_2O_8$, 0.3 mmu·error); 161.0605 (calcd for $C_{10}H_9O_2$, –0.2 mmu error); 121.0658 (calcd for $C_8H_9O$, –0.4 mmu error). $^1$H NMR (CDCl$_3$): amino or hydroxy acid unit δ (carbon position, multiplicity; J in Hz) 7,8-epoxy-5-hydroxy-6-methyl-8phenyl-2-octenoic acid (A) 5.71 (2, dd; 15.4 and 1.3), 6.70 (3, ddd; 15.4, 10.2 and 5.0), 2.45 (4, m), 2.55 (4, m), 5.18 (5, ddd; 11.3, 4.8 and 2.0), 1.79 (6, m), 1.14 (6-Me, d; 7.0), 2.92 (7, dd; 7.7 and 2.0), 3.68 (8, d; 2.0), 7.24 (10/14, m), 7.34–7.39 (11/12/13, m); leucic acid (D) 4.82 (2, dd; 10.1 and 3.7), 1.70 (3, m), 1.33 (3, m), 1.70 (4, m), 0.86 (5, d; 6.4), 0.84 (5', d; 6.4); 3-amino-2-methylpropionic acid (C) 2.68 (2, m), 1.23 (2-Me, d; 7.3), 3.39 (3-H$_2$, m), 7.02 (3-NH,brt; 6.0); O-methyltyrosine (B) 4.79 (2, ddd; 8.1, 7.0 and 5.7), 5.55 (2-NH, d; 8.1), 3.07 (3, dd; 14.5 and 7.0), 3.13 (3, dd; 14.5 and 5.7), 7.10 (5/9, d; 8.6), 6.81 (6/8, d; 8.6), 3.78 (7-OCH$_3$, s). $^{13}$C NMR (CDCl$_3$): unit δ (carbon position) A 165.1 (1), 125.1 (2), 141.1 (3), 36.7 (4), 76.0 (5), 40.7(6), 13.6 (6-Me), 63.0 (7), 59.0 (8), 136.7 (9), 125.6 (10/14), 128.7 (11/13), 128.5 (12); D 170.6(1), 71.3 (2), 39.4 (3), 24.5 (4), 21.3 (5), 22.9 (5'); C 176.0 (1), 38.1 (2), 14.2 (2-Me), 40.7 (3); B 171.1 (1), 53.9 (2), 35.3 (3), 131.0 (4), 130.2 (5/9), 114.1 (6/8), 158.6 (7), 55.2 (7-OCH$_3$).

Cryptophycin 3

$[\alpha]_D$+20.3°(MeOH, c 1.13); UV $\lambda_{max}(\epsilon)$ 206 (51,700), 218 (31,200), 230 (22,900), 246 (18,800), 280 (3,230); CD $[\theta]_{205}$+50,000, $[\theta]_{212}$–390, $[\theta]_{218}$–47,200, $[\theta]_{233}$–100, $[\theta]_{251}$+33,400, $[\theta]_{271}$+33,400, $[\theta]_{271}$+4,310. IR (CHCl$_3$) $\nu_{max}$ 3417, 2926, 1742, 1721, 1676, 1499, 1336 cm$^{-1}$. EIMS m/z (rel intensity) 638/640 (2/0.7, M$^+$), 412/414 (63/19), 280/282 (15/5), 227 (100), 195 (63), 91 (98); high resolution EIMS m/z 638.2764 (calcd for $C_{35}H_{43}ClN_2O_7$, –0.5 mmu error), 412.1516 (calcd for $C_{20}H_{27}ClNO_6$, 1.1 mmu error), 227.1293 (calcd for $C_{15}H_{17}NO$, 1.0 mmu error). $^1$H NMR (CDCl$_3$): amino or hydroxy acid unit δ (carbon position, multiplicity; J in Hz) 5-hydroxy-6-methyl-8-phenyl-2,7-octadienoic acid (A) 5.77 (2, d; 15.5), 6.68 (3, ddd; 15.5, 9.5 and 5.3), 2.37 (4, m), 2.54 (4, m), 5.01(5, ddd; 11.4, 6 and 1.5), 2.56 (6, m), 1.14 (6-Me, d; 7.0), 6.01 (7, dd; 15.8 and 8.8), 6.41 (8, d; 15.8), 7.28–7.34 (10/11/13/14, m), 7.23 (12, m); leucic acid (D) 4.84 (2, dd; 10.1 and 3.6), 1.62 (3, m), 1.36 (3, m), 1.62 (4, m), 0.77 (5, d; 6.5), 0.73 (5', d; 6.3); 3-amino-2-methylpropionic acid (C) 2.71 (2, m), 1.22 (2-Me, d; 7.3), 3.28 (3, dt; 13.5 and 7.0), 3.50 (3, ddd; 13.5, 4.9 and 4), 6.93 (3-NH, brt; 6.3); 3-chloro-4-methoxyphenylalanine (B) 4.82 (2, m), 5.64 (2-NH, d; 8.8), 3.05 (3, dd; 14.5 and 7.0), 3.13 (3, dd; 14.5 and 5.5), 7.22 (5, d; 2.2), 3.87 (7-OCH$_3$, s), 6.84 (8, d; 8.5), 7.08 (9, dd; 8.5 and 2.2). $^{13}$C NMR (CDCl$_3$): unit δ (carbon position) A 165.4 (1), 125.2 (2), 141.4 (3), 36.5 (4), 77.1 (5), 42.3 (6), 17.3 (6-Me), 130.1(7), 130.0 (8), 136.7 (9), 126.1 (10/14), 128.6 (11/13), 128.4 (12); D 170.1 (1), 71.6 (2), 39.5 (3), 24.5 (4), 21.2 (5), 22.7 (5'); C 175.6 (1), 38.3 (2), 14.0 (2-Me), 41.2 (3); B 170.9 (1), 53.5 (2), 35.1 (3), 129.8 (4), 131.0 (5), 122.4 (6), 154.0 (7), 56.1 (7-OCH$_3$), 112.2 (8), 127.6 (9).

Cryptophycin 4

$[α]_D$+36.7°(MeOH, c 1.93); UV) $λ_{max}(ε)$ 206 (41,800), 228 (25,000), 240 (21,200), 248 (22,500), 280 (3,000), 290 (1,230); CD $[θ]_{205}$+63,900, $[θ]_{211}$+3,040, $[θ]_{218}$−71,900, $[θ]_{229}$−11,700, $[θ]_{234}$−130, $[θ]_{252}$+47,500, $[θ]_{270}$+5,400. IR (CHCl$_3$)$ν_{max}$ 3410, 2962, 2917, 1741, 1718, 1678, 1511, 1251 cm$^{-1}$. EIMS m/z (rel intensity) 604 (2, M$^+$), 378 (74), 246 (11), 227 (46), 161 (100), 91 (96); high resolution EIMS m/z 604.3127 (calcd for C$_{35}$H$_{44}$N2O$_7$, 2.2 mmu error), 378.1910 (calcd for C$_{20}$H$_{28}$NO$_6$, 0.7 mmu error), 227.1293 (calcd for C$_{15}$H$_{17}$NO, 1.7 mmu error), 161.0605 (calcd for C$_{10}$H$_9$O$_2$, −0.2 mmu error). $^1$H NMR (CDCl$_3$): amino or hydroxy acid unit δ (carbon position, multiplicity; J in Hz) S-hydroxy-6-methyl-8phenyl-2,7-octadienoic acid (A) 5.74 (2, dd; 15.3 and 1.2), 6.71 (3, ddd; 15.3, 10.3 and 5.0), 2.37 (4, m), 2.53 (4, m), 5.03 (5, ddd; 11.2, 6.4 and 2.0), 2.55 (6, m), 1.13 (6-Me, d; 6.8), 6.01 (7, dd; 15.8 and 8.8), 6.40 (8, d; 15.8), 7.28–7.37 (10/11/13/14, m), 7.22 (12, m); leucic acid (D) 4.84 (2, dd; 10.1 and 3.6), 1.65 (3, m), 1.34 (3, m), 1.65 (4, m), 0.75 (5, d; 6.5), 0.72 (5', d; 6.3); 3-amino-2-methylpropionic acid (C) 2.69 (2, m), 1.22 (2-Me, d; 7.5), 3.39 (3-H$_2$, m), 7.03 (3-NH, brt; 6.0); O-methyltyrosine (B) 4.79 (2, m), 5.61 (2-NH, d; 7.8), 3.08 (3, dd; 14.5 and 7.0), 3.13 (3, dd; 14.5 and 5.3), 7.11 (5/9, d; 8.8), 6.81 (6/8, d; 8.8), 3.78 (7-OCH$_3$, s). $^{13}$C NMR (CDCl$_3$): unit δ (carbon position) A 165.3 (1), 125.1 (2), 141.5 (3), 36.5 (4), 77.1(5), 42.3 (6), 17.3 (6-Me), 130.1 (7), 131.8 (8), 136.7 (9), 126.2 (10/14), 128.7 (11/13), 127.6 (12); D 170.8 (1), 71.6 (2), 39.5 (3), 24.5 (4), 21.2 (5), 22.7 (5'); C 175.9 (1), 38.2 (2), 14.2 (2-Me), 40.9 (3); B 171.2 (1), 53.8 (2), 35.3 (3), 131.0 (4), 130.2 (5/9), 114.1 (6/8), 158.6 (7), 55.2 (7-OCH$_3$).

Cryptophycin 5

$[α]_D$+36.0° (MeOH, c 0.55); UV $λ_{max}(ε)$ 206 (45,600), 218 (37,700), 280 (3,790), 286 (3,480), 325 (2,080); CD $[θ]_{203}$ +7,710, $[θ]_{206}$+29,000, $[θ]_{210}$+21,400, $[θ]_{222}$+59,800, $[θ]_{234}$+12,800, $[θ]_{241}$+13,700. IR (CHCl$_3$) $ν_{max}$ 3426, 2958, 1728, 1672, 1502, 1259 cm$^{-1}$. EIMS m/z (rel intensity) 686/688 (0.1510.05), 655/657 (1/0.3), 654/656 (1.5/0.5), 311/313 (75/27), 195 (66), 155 (54), 121 (51), 91 (100); high resolution EIMS m/z 686.2983 (calcd for C$_{36}$H$_{47}$ClN$_2$O$_9$, −1.3 mmu error). $^1$H NMR (CDCl$_3$): amino or hydroxy acid unit δ (carbon position, multiplicity; J in Hz) 7,8-epoxy-5-hydroxy-6-methyl-8-phenyl-2-octenoic acid (A) 5.87 (2, d; 15.3), 6.72 (3, dt; 15.3 and 6.8), 2.60 (4, m), 2.52 (4, ddd; 15.2, 7.8, and 6.8), 5.11 (5, ddd; 12.3, 7.8, and 7.1), 1.87 (6,m), 1.12 (6-Me, d; 7.1), 2.91 (7, dd; 7.3 and 2.1), 3.70 (8, d; 2.1), 7.24 (10/14, brd; 7.4), 7.29–7.36 (11/12/13, m); leucic acid (D) 4.09 (2, m), 2.86 (2-OH, brd, 6.1), 1.83 (3, m), 1.42 (3, m), 1.86 (4, m), 0.90 (5, d; 6.6), 0.87 (5', d; 6.8); 3-amino-2-methylpropionic acid (C) 3.64 (I—OCH$_3$, s), 2.60 (2, m), 1.07 (2-Me, d; 7.3), 3.27 (3, ddd; 13.5, 8.0 and 5.5), 3.39 (3, m), 6.32 (3-NH, t; 5.4); 3-chloro-4-methoxyphenylalanine (B) 4.59 (2, dt; 6 and 7.5), 6.30 (2-NH, d; 7.5), 2.95 (3, dd; 13.6 and 7.5), 3.0 (3, dd; 13.6 and 6.0), 7.2 (5, d; 2.1), 3.86 (7-OCH$_3$, s), 6.84 (8, d; 8.5), 7.05 (9, dd, 8.5; 2.1), $^{13}$C NMR (CDCl$_3$): unit δ (carbon position) A 164.8 (1), 126.5 (2), 139.2 (3), 34.4 (4), 75.5 (5), 39.2 (6), 12.9 (6-Me), 63.3 (7), 58.7 (8), 136.8 (9), 125.7 (10/14), 128.6 (11/13), 128.4 (12); D 175.1 (1), 69.2 (2), 43.2 (3), 24.3 (4), 21.2 (5), 23.2 (5'); C 175.4 (1), 51.9 (1-OMe), 39.1 (2), 14.7 (2-Me), 41.6 (3); D 170.6 (1), 54.6 (2), 37.4 (3), 129.5 (4), 131.0 (5), 122.4 (6), 154.1(7), 56.1 (7-OMe), 112.2 (8), 128.4 (9).

Cryptophycin 6

$[α]_D$+17.1°)(MeOH, c 1-1); UV$λ_{max}(ε)$ 206 (40,000), 218 (30,100), 228 (21,400), 282 (2,430); CD $[θ]_{203}$+37,700, $[θ]_{210}$−5,430, $[θ]_{213}$−1,260, $[θ]_{221}$+24,100, $[θ]_{232}$+8,480, $[θ]_{240}$+13,400, $[θ]_{254}$+790. IR (CHCl$_3$) $ν_{max}$ 3425, 3006, 2956, 1726, 1672, 1641, 1502, 1462, 1259 cm$^{-1}$. FABMS (thioglycerol) m/z, (rel intensity) 573/575 (13/6) [M-H$_2$O]$^+$, 217 (26), 91 (100). $^1$H NMR(CDCl$_3$): amino or hydroxy acid unit δ (carbon position, multiplicity; J in Hz) 5,7,8-trihydroxy-6-methyl-8-phenyl-2-octenoic acid (A) 5.92 (2, dt; 15.0 and 1.5), 6.94 (3, dt; 15 and 7.5), 2.51 (4, m), 2.64 (4, m), 3.97 (5, ddd; 9.3, 6.5 and 4.5), 2.03 (6, m), 1.10 (6-Me , d; 6.5), 3.70 (7, dd; 9.0 and 7.5), 4.64 (8, d; 7.5), 7.33–7.39 (10/11/13/14, m), 7.28 (12, tt; 6.5 and 2.0); 3-chloro-4-methoxyphenylalanine (B) 4.60 (2, td; 8.0 and 6.0), 6.09 (2-NH, brd; 8.0), 2.96 (3, dd; 13.8 and 8.0), 3.02 (3, dd; 13.8 and 6.0), 7.22 (5, d; 2.0), 3.86 (7-OCH$_3$, s), 6.84 (8, d; 8.5), 7.07 (9, dd;. 8.5 and 2.0) 3-amino-2-methylpropionic acid (C) 3.63 acid (C) 3.63 (1-OCH$_3$,s), 2.58 (2, m), 1.07 (2-Me, d; 7.0), 3.24 (3, ddd; 13.8, 8 and 6.5), 3.41 (3, ddd; 13.8, 6.5 and 4.8), 6.21 (3-NH, brt; 6.5). $^{13}$C NMR (CDCl$_3$): unit δ (carbon position) A 165.2 (1), 125.6 (2), 141.3 (3), 36.9 (4), 82.5 (5), 46.3 (6), 14.3 (6-Me), 85.1(7), 84.8 (8), 140.9 (9), 125.8 (10/14), 128.6 (11/13), 127.8 (12); B 170.6 (1), 54.5 (2), 37.3 (3), 129.6 (4), 131.0 (5), 122.5 (6), 154.1 (7), 56.1 (7-OCH$_3$), 112.2 (8), 128.5 (9) C 52.0 (1-OCH$_3$), 175.4 (1), 39.2 (2), 14.7 (2-Me), 41.6 (3).

Cryptophycin 7

$[α]_D$−51.9° (MeOH, c 0.89); UV $λ_{max}(ε)$ 206 (23,400), 220 (14,900), 282 (1,670); CD $[θ]_{202}$+35,400, $[θ]_{206}$−1,730, $[θ]_{211}$−19,200, $[θ]_{220}$−15,800, $[θ]_{232}$+29,000, $[θ]_{263}$+2,040. IR (CHCl$_3$) $ν_{max}$ 3426, 2946, 1732, 1675, 1501, 1258 cm$^{-1}$. EIMS m/z (rel intensity) 455/457 (1/0.3, [M-2H$_2$O]$^+$), 105 (100), 77 (98); FABMS m/z (magic bullet matrix) 496/498 [M-H$_2$O+Na]$^+$, (thioglycerol matrix) 474/476 [M-H$_2$O1+H]$^+$. $^1$H NMR (CD$_3$OHD): amino or hydroxy acid unit δ (carbon position, multiplicity; J in Hz) 5,7,8-trihydroxy-6-methyl-8-phenyl-2-octenoic acid (A) 6.06 (2, ddd; 15.5, 1.3 and 1.0), 6.80 (3, dt; 15.5 and 7.5), 2.49 (4, m), 2.59 (4, m), 3.92 (5, ddd; 9.5, 6.3 and 4.7), 1.95 (6, m), 1.08 (6-Me, d; 6.7), 3.59 (7, dd; 9.0 and 7.8), 4.56 (8, d; 7.8), 7.37 (10/14, brd; 7.3), 7.31 (11/13, brt; 7.3), 7.24 (12, tt; 7.3 and 1.5); 3-chloro-4-methoxyphenylalanine (B) 4.52 (2, dd; 6.9 and 5.0), 2.93 (3, dd; 13.8 and 6.9), 3.15 (3, dd; 13.8 and 5.0), 7.20 (5, d; 2.2), 3.78 (7-OCH$_3$, s), 6.88 (8, d; 8.4), 7.08 (9, dd; 8.4 and 2.2). $^{13}$C NMR (CD$_3$OD): unit δ (carbon position) A 167.4 (1), 127.6 (2), 140.9 (3), 37.9 (4), 84.0 (5), 47.6 (6), 14.4 (6-Me), 86.0 (7), 85.8 (8), 142.9 (9), 127.1 (10/14), 129.3 (11/13), 128.5 (12); B 177.6 (1), 57.3 (2), 38.2 (3), 132.8 (4), 132.1 (5), 122.9 (6), 155.0 (7), 56.5 (7-OCH$_3$), 113.2 (8), 130.1 (9).

EXAMPLE 6

Synthesis of Cryptophycin Derivatives

Cryptophycin 8

To a solution of 3.8mg of Cryptophycin 1 in 1.5 mL of 2:1 1,2-dimethoxyethane/water was added 9 μL 1N HCl. The solution was allowed to stir at room temperature for 4 h, neutralized with potassium carbonate, and evaporated. The residue was partitioned between water and CH$_2$Cl$_2$. The CH$_2$Cl$_2$-soluble material was purified by reversed-phase HPLC to obtain 3.3 mg of pure Cryptophycin 8.

EIMS m/z (relative intensity) 690/692/694 (0.8/0.5/0.2). High resolution EIMS m/z 690.2533 (calcd for C$_{35}$H$_{44}$Cl$_2$N$_2$O$_8$, −5.8 mmu error). $^1$H NMR (CDCL$_3$): amino or hydroxy acid unit δ(carbon position, multiplicity; J in Hz) 8chloro-5, 7-dihydroxy-6-methyl-8-phenyl-2-octenoic acid (A) 5.79 (2, d; 15.4), 6.69 (3, ddd; 15.4, 9.7 and 5.6), 2.68 (4, ddt; 14.0, 5.5 and 1.8), 2.38 (4, m),5.11 ( ddd; 10.8, 8.6 and 1.8), 2.51 (6, m), 1.05 (6-Me, d; 7.0), 4.01

(7, dd; 9.6 and 4.65 (8, d; 9.6), 7.36–7.41 (10/11/12/13/14, m); leucic acid (D) 4.92 (2, dd; 10.1 and 3.5), 1.76 (3/4, m), 1.45 (3, m), 0.94 (5, d; 6.6), 0.94 (5', d; 6.4); 3-amino-2-methylpropionic acid (C) 2.73(2, m), 1.22 (2-Me, d; 7.2), 3.25 (3, ddd; 13.6, 6.8 and 6.1), 3.54 (3, ddd; 13.5, 6.1 and 3.4), 6.91(3-NH, brt; 6. 1); 3-chloro-4methoxyphenylalanine (B) 4.82 (2, ddd; 8.8, 7.2 and 5.6), 5.64 (2-NH, d; 8.8), 3.03 (3, dd; 15.4 and 7.2), 3.16 (3, dd; 15.4 and 5.6), 7.23 (5, d; 2.2), 3.88 (7-OCH$_3$, s), 6.85 (8, d; 8.5), 7.09 (9, dd; 8.5 and 2.2).

Cryptophycin 9

To a solution of 10 mg of Cryptophycin 1 in 1 mL dry methanol was added 10 μL methanolic HCl (obtained by treating 1.25 g thionyl chloride with 25 mL MeOH). After stirring for 4 h the solvent was removed in vacuo and the sample was left under vacuum for 12 h. Reversed-phase HPLC gave 8 mg of pure Cryptophycin 9.

$^1$H NMR (CDCl$_3$): amino or hydroxy acid unit δ (carbon position, multiplicity; J in Hz); 5,7-dihydroxy-8-methoxy-6-methyl-8-phenyl-2-octenoic acid (A) 5.76 (2, d; 15.5), 6.67 (3, ddd; 15.5, 9.5 and 5.6), 2.34 (4, ddd; 14.1, 11.1 and 9.5), 2.62 (4, dddd; 14.1, 5.6, 1.8 and 1.5), 5.09 (5, ddd; 11.1, 7.8 and 1.8), 2.24 (6, dqd; 7.8, 7.0 and 2.2), 1.03 (6-Me, d; 7.0), 3.71 (7, dd; 8.3 and 2.2), 4.03 (8, d; 8.3), 3.20 (8-OCH$_3$, s), 7.31–7.40 (10/11/12/13/14, m); leucic acid (D) 4.86 (2, dd; 9.8 and 3.5), 1.71 (3/4, m), 1.41 (3, m), 0.89 (5/5', d; 6.4); 3-amino-2-methylpropionic acid (C) 2.71 (2, ddq; 6.8, 3.9 and 7.2), 1.21 (2-Me, d; 7.2), 3.23 (3, ddd; 13.5, 6.8 and 6.0), 3.52 (3, ddd; 13.5, 6.0 and 3.9), 6.90 (3-NH, brt; 6.0); 3-chloro-4-methoxyphenylalanine (B) 4.82 (2, ddd; 8.8, 7.4 and 5.7), 5.66 (2-NH, d; 8.8), 3.02 (3, dd; 14.4, 7.4), 3.15 (3, dd; 14.4 and 5.5), 7.23 (5, d; 2.2), 3.87 (7-OCH$_3$, s), 6.84 (8, d; 8.5), 7.08 (9, dd; 8.5 and 2.2).

Cryptophycin 10

To a stirred solution of 7 mg of Cryptophycin 9 in 1 mL of acetone and 0.3mL water was added 8 μL of 2N NaOH. After stirring for 4 h the solution was neutralized to pH 7 with 1N HCl and the solvent was removed under reduced pressure. The residue was subjected to reversed-phase HPLC using 7:3 MeOH/H$_2$O to yield pure Cryptophycin 10 (5 mg).

$^1$H NMR (CD$_3$OD): amino or hydroxy acid unit δ (carbon position, multiplicity; J in Hz); 5,7-dihydroxy-8-methoxy-6-methyl-8-phenyl-2-octenoic acid (A) 5.99 (2, dt; 15.4 and 1.3), 6.82 (3, dt; 15.4 and 7.3), 2.30 (4, m), 2.50 (4, m), 3.66 (5, td; 7.8 and 3.5), 2.05 (6, d pentet; 1.8 and 7.0), 0.96 (6-Me, d; 7.0), 4.04 (7, dd; 8.8 and 2.0), 4.01 (8, d; 8.8), 3.12 (8-OCH$_3$, s), 7.26–7.36 (10/11/12/13/14, m); 3-amino-2-methylpropionic acid (C) 2.50 (2, m), 1.02 (2-Me, d; 7.3), 3.16 (3, dd; 13.4 and 6.9), 3.82 (3, dd; 13.4 and 6.6); 3-chloro-4-methoxyphenylalanine (B) 4.57 (2, dd; 8.5 and 6.5), 2.82 (3, dd; 13.9 and 8.6), 3.03 (3, dd; 13.9 and 6.5), 7.25 (5, d; 2.2), 3.82 (7-OCH$_3$, s), 6.96 (8, d; 8.6), 7.13 (9, dd; 8.6 and 2.2). $^{13}$C NMR (CD$_3$OD): δ 179.5, 173.4, 168.2, 155.4, 143.7, 141.7, 131.9, 131.7, 129.8, 129.3 (2C), 129.2 (2C), 128.8, 126.2, 123.2, 113.4, 85.9, 74.5, 74.1, 56.8, 56.6, 56.3, 43.3, 41.2, 40.2, 38.8, 38.0, 15.5, 9.9.

Cryptophycin 12

To a solution of 5mg of Cryptophycins 1, 5 or 8 in 1mL of 4:1 acetone/water was added 15 μL of 2N NaOH. After stirring at room temperature for 5 h, the reaction mixture was neutralized to pH 7 with 1N HCl and evaporated. The CH$_2$Cl$_2$-soluble material was passed through a small silica-cartridge with CH$_2$Cl$_2$, 1:1 EtOAc/CH$_2$Cl$_2$, and EtOAc. The fraction eluted with EtOAc contained pure Cryptophycin 12.

$^1$H NMR (CD$_3$OD): amino or hydroxy acid unit δ (carbon position, multiplicity; J in Hz); 5,7,8-trihydroxy-6-methyl-8-phenyl-2-octenoic acid (A) 6.07 (A) (2, ddd; 15.5, 1.3 and 1.2), 6.40 (3, dt; 15.5 and 7.3), 2.49 (4, m), 2.60 (4, m), 3.92 (5, ddd; 9.3, 6.7 and 4.5), 1.94 (6, m), 1.07 (6-Me, d; 6.6), 3.61 (7, dd; 8.9 and 7.6), 4.56 (8, d; 7.6), 7.36 (10/14, dd; 7.4 and 1.5), 7.32 (11/13, brt; 7.5 ), 7.25 (12, m); 3-amino-2-methylpropionic acid (C) 2.54 (2, ddq; 7.0, 6.6 and 7.0), 1.02 (2-Me, d; 7.0), 3.14 (3, dd; 13.5 and 7.0), 3.42 (3, dd; 13.4 and 6.6); 3-chloro-4-methoxyphenylalanine (B) 4.57 (2, dd; 8.4 and 6.7), 2.83 (3, dd; 13.8 and 8.4), 3.02 (3, dd; 13.8 and 6.6), 7.25 (5, d; 2.1), 3.82 (7-OCH$_3$, s), 6.95 (8, d; 8.5), 7.12 (9, dd; 8.5 and 2. 1). Methylation of Cryptophycin 12 with diazomethane gave Cryptophycin 6.

Cryptophycin 14

To a solution of 3 mg of Cryptophycin 6 in 1mL of 3:1 acetone/H$_2$O was added 5 μL of 2N NaOH. After stirring for 5 h, the reaction mixture was neutralized to pH 7 with 1N HCl and then evaporated to dryness. The residue was subjected to reversed-phase HPLC to give 2.4mg of Cryptophycin 14.

$^1$H NMR (CD$_3$OD): amino or hydroxy acid unit δ (carbon position, multiplicity; J in Hz); 5-hydroxy-6-methyl-8-phenyl-2,7-octadienoic acid (A) 5.98 (2, d; 15.3), 6.78 (3, dt; 15.3 a-nd 7.5), 2.35 (4, m), 3.64 (5, td; 7.2 and 4.8), 2.47 (6, m), 1. 14 (6-Me, d; 6.9), 6.22 (7, dd; 15.9 and 8.1), 6.39 (8, d, 15.9), 7.24–7.36 (10/11/12/13/14, m); 3-amino-2-methylpropionic acid (c) 2.35 (2, m), 1.02 (2-Me, d; 6.9), 3.18 (3, dd; 13.2 and 6.6), 3.36 (3, dd; 13.2 and 4.5); 3-chloro-4-methoxyphenylalanine (B) 4.58 (2, dd; 8.7 and 6.3), 2.80 (3, dd; 13.8 and 9.0), 3.05 (3, dd; 13.8 and 6.3), 7.25 (5, d; 2.1), 3.82 (7-OCH$_3$, s), 6.95 (8, d; 8.4), 7.13(9, dd; 8.4 and 2.1). cl EXAMPLE 10

Analysis of Microtubule Depolymerizing Activity of Cryptophycin

Materials

Vinblastine, cytochalasin B, tetramethylrhodamine isothiocyanate (TRITC)-phalloidin, sulforhodamine B (SRB) and antibodies against β-tubulin and vimentin were obtained from the Sigma Chemical Company. Basal Medium Eagle containing Earle's salts (BME) was from Gibco and Fetal Bovine Serum (FBS) was purchased from Hyclone Laboratories.

Cell Lines

The Jurkat T cell leukemia line and A-10 rat aortic smooth muscle cells were obtained from the American Type Culture Collection and were cultured in BME containing 10% FBS and 50 μg/ml gentamycin sulfate. Human ovarian carcinoma cells (SKOV3) and a sub-line which has been selected for resistance to vinblastine (SKVLB1) were a generous gift from Dr. Victor Ling of the Ontario Cancer Institute. Both cell lines were maintained in BME containing 10% FBS and 50 μg/ml gentamycin sulfate. Vinblastine was added to a final concentration of 1 μg/ml to SKVLB1 cells 24 hours after passage to maintain selection pressure for P-glycoprotein-overexpressing cells.

Cell Proliferation and Cycle Arrest Assays

Cell proliferation assays were performed as described by Skehan et al.[11] For Jurkat cells, cultures were treated with the indicated drugs as described in Skehan[11] and total cell numbers were determined by counting the cells in a hemacytometer. The percentage of cells in mitosis was determined by staining with 0.4% Giemsa in PBS followed by three rapid washes with PBS. At least 1000 cells per treatment were scored for the presence of mitotic figures and the mitotic index was calculated as the ratio of cells with mitotic figures to the total number of cells counted.

Immunofluorescence Assays

A-10 cells were grown to near-confluency on glass coverslips in BME/10% FBS. Compounds in PBS were added to the indicated final concentrations and cells were incubated for an additional 24 hours. For the staining of microtubules and intermediate filaments, the cells were fixed with cold methanol and incubated with PBS containing 10% calf serum to block nonspecific binding sites. Cells were then incubated at 37° C. for 60 min with either monoclonal anti-β-tubulin or with monoclonal anti-vimentin at dilutions recommended by the manufacturer. Bound primary antibodies were subsequently visualized by a 45-minute incubation with fluorescein-conjugated rabbit antimouse IgG. The coverslips were mounted on microscope slides and the fluorescence patterns were examined and photographed using a Zeiss Photomicroscope Ill equipped with epifluorescence optics for fluorescein. For staining of microfilaments, cells were fixed with 3% paraformaldehyde, permeabilized with 0.2% Triton X-100 and chemically reduced with sodium borohydride (1mg/ml). PBS containing 100 nM TRITC-phalloidin was then added and the mixture was allowed to incubate for 45 min at 37° C. The cells were washed rapidly three times with PBS before the coverslips were mounted and immediately photographed as described above.

Effects of cryptophycins and vinblastine on Jurkat cell proliferation and cell cycle Dose-response curves for the effects of cryptophycin compounds and vinblastine on cell proliferation and the percentage of cells in mitosis are indicated in FIGS. 2A and 2B, respectively. Less than 3% of untreated cells displayed mitotic figures. Both the cryptophycin compounds and vinblastine caused dose-dependent increases in the percentage of cells observed in mitosis. The increase in the mitotic index was closely correlated with decreases in cell proliferation, i.e. the concentrations of both cryptophycin compounds and vinblastine that caused 50% of the cells to accumulate in mitosis was virtually the same as the concentration which inhibited cell proliferation by 50%. The $IC_{50}$s for the cryptophycin compounds and vinblastine for these effects were 0.2 and 8 nM, respectively.

Effects of cytochalasin B, vinblastine and cryptophycins on the cytoskeleton

Aortic smooth muscle (A-10) cells were grown on glass coverslips and treated with PBS, 2 μM cytochalasin B, 100 nM vinblastine or 10 nM cryptophycin compounds. After 24 hours, microtubules and vimentin intermediate filaments were visualized by indirect immunofluorescence and microfilaments were stained using TRITC-phalloidin. The morphological effects of each drug were examined. Untreated cells displayed extensive microtubule networks complete with perinuclear microtubule organizing centers. Vimentin intermediate filaments were also evenly distributed throughout the cytoplasm, while bundles of microfilaments were concentrated along the major axis of the cell. Cytochalasin B caused complete depolymerization of microfilaments along with the accumulation of paracrystalline remnants. This compound did not affect the distribution of either microtubules or intermediate filaments. Both vinblastine and the cryptophycin compound caused marked depletion of microtubules. Neither compound affected microfilament organization; however, vimentin intermediate filaments collapsed, forming concentric rings around the nuclei of cells treated with either vinblastine or a cryptophycin compound.

Effects of cryptophycins and vinblastine on taxol-stabilized microtubules

A-10 cells were treated for 3 hours with 0 or 10 μM taxol before the addition of PBS, 100 nM vinblastine or 10 nM cryptophycin compound. After 24 hours, microtubule organization was examined by immunofluorescence as described above. Compared with those in control cells, microtubules in taxol-treated cells were extensively bundled, especially in the cell polar regions. As before, vinblastine caused complete depolymerization of microtubules in non-pretreated cells. However, pretreatment with taxol prevented microtubule depolymerization in response to vinblastine. Similarly, taxol pretreatment completely stabilized microtubules against cryptophycin-induced depolymerization.

Reversibility of microtubule depolymerization by vinblastine and cryptophycin

A-10 cells were treated with either 100 nM vinblastine or 10 nM cryptophycins for 24 hr, resulting in complete microtubule depolymerization. The cells were then washed and incubated in drug-free medium for periods of 1 hour or 24 hours. Microtubules repolymerized rapidly after the removal of vinblastine, showing significant levels of microtubules after 1 hour and complete morphological recovery by 24 hour. In contrast, microtubules did not reappear in cells treated with cryptophycin compounds at either 1 hour or 24 hours after removal of the compound.

Figure 3:
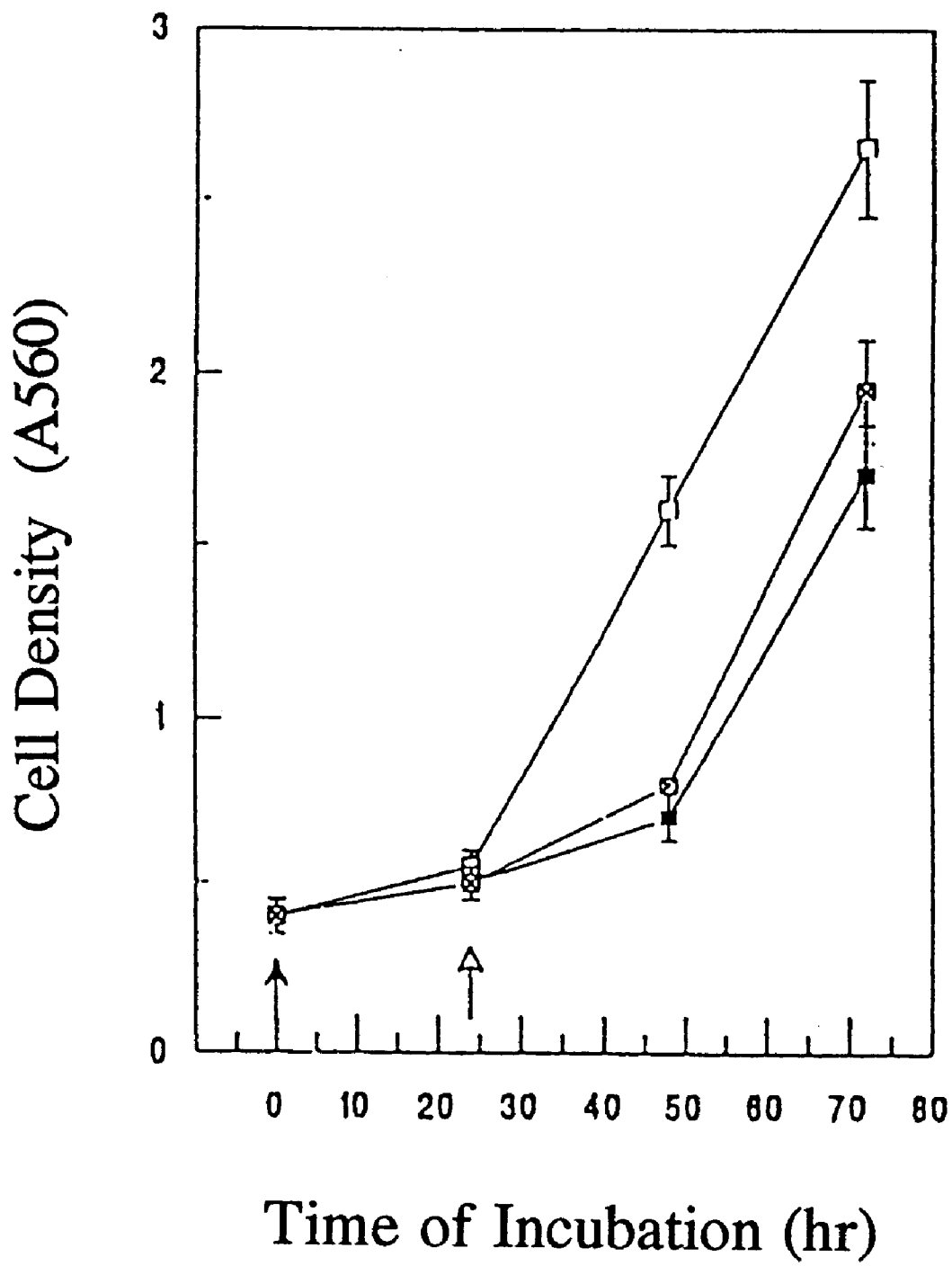
FIG. 3 graphically presents the reversibility of the effects of vinblastine, cryptophycins and taxol on cell growth. SKOV3 cells were treated with 0.1 nM vinblastine (□), 0.1 nM cryptophycins (■) or 1 nM taxol (⊠) at time=0. These concentrations inhibited cell growth by 50% for each compound. After 24 hours the cells were washed and incubated in drug-free medium for the time indicated. The cell density was determined by sulforhodamine B (SRB) staining as described in the Experimental section, and is expressed as the mean±sd absorbance at 560 nm for triplicate samples in one of three experiments.

Reversibility of cryptophvcins- vinblastine- and taxol-inhibition of cell proliferation SKOV3 cells were treated for 24 hours with previously determined $IC_{50}$ doses of vinblastine, cryptophycin compounds or taxol (i.e. values determined in experiments summarized in Table 3). During this time the cell density increased from 0.4 to 0.5±0.05 absorbance units (FIG. 3), indicating a 25% increase in cell number for all three treatments. Removal of the drugs resulted in rapid growth of the vinblastine-treated cells, such that their numbers were increased approximately 3-fold in 24 hours. In contrast, cells treated with cryptophycin compounds or taxol remained arrested, increasing only 0.2- to 0.4-fold in the 24 hours following removal of the drug. The proliferative capacity of cryptophycins or taxol-treated cells was subsequently restored since the cells then doubled in the next 24 hours.

Effects of combinations of vinblastine and cryptophycins on cell proliferation

Figure 4:
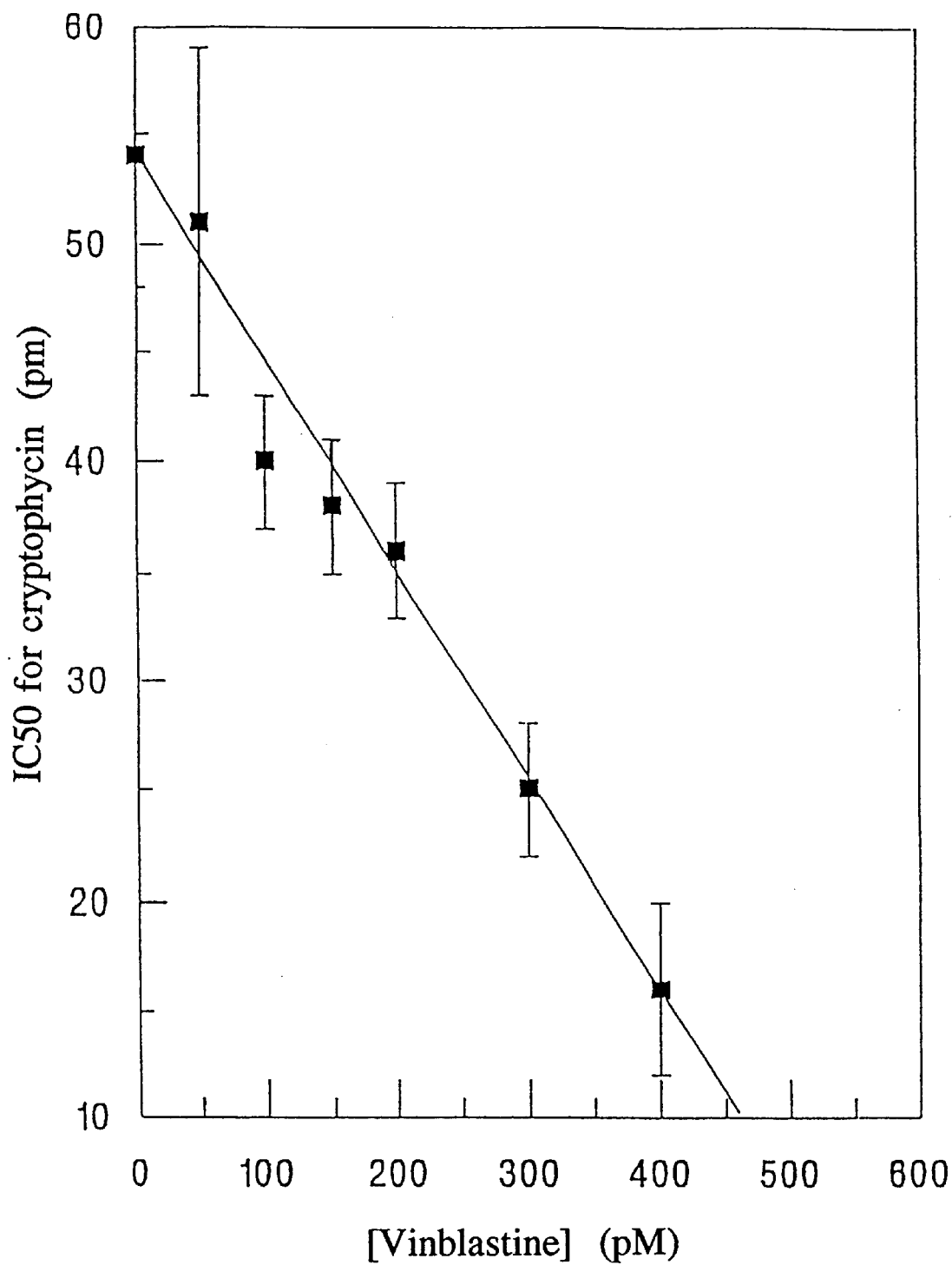
FIG. 4 provides Isobolograms for combinational effects of vinblastine and cryptophycins on cell proliferation. SKOV3 cells were treated with vinblastine (0–600 pM) and/or cryptophycins (1–100 pM) for 48 hours. Cell numbers were then determined by SRB staining as described in the Experimental section, and the $IC_{50}$s (■) and the line of additivity (—) for combinations of vinblastine and cryptophycin compounds. Values represent the means for two experiments each containing triplicate samples.

SKOV3 cells were treated with combinations of cryptophycins and vinblastine for 48 hours. The percentages of surviving cells were then determined and the $IC_{50}$s for each combination was calculated. The effects of these combinational treatments, as well as single drug treatments, are depicted as an isobologram (FIG. 4). The $IC_{50}$s for combinations of cryptophycin compounds and vinblastine fell very close to the line of additivity, indicating that these two drugs induce only additive inhibitions of cell proliferation.

Toxicity of cryptophycins, vinblastine and taxol toward SKOV3 and SKVLB1 cells

SKVLB1 cells are resistant to natural product anticancer drugs because of their over expression of P-glycoprotein[12]. The abilities of taxol, vinblastine and cryptophycin compounds to inhibit the growth of SKOV3 and SKVLB1 cells are summarized in Table 3. Taxol caused dose-dependent inhibition of the proliferation of both cell lines with $IC_{50}$s for SKOV3 and SKVLB1 cells of 1 and 8000nM, respectively. Vinblastine also inhibited the growth of both cell lines, with $IC_{50}$s of 0.35 and 4200 nM for SKOV3 and SKVLB1 cells, respectively. Cryptophycins demonstrated $IC_{50}$s of 7 and 600 pM for SKOV3 and SKVLB1 cells, respectively. The resulting resistance factors for SKVLB1 cells to the compounds are calculated as the $IC_{50}$ for SKVLB1. $IC_{50}$s for SKOV3 cells are also indicated in Table 3.

TABLE 3

Cells were treated with varying concentrations of the compounds indicated below for 48 hours. Cell numbers were then determined as indicated in the Methods section and the $IC_{50}$ for each compound was calculated. Values represent the mean ± SEM for three experiments.

| | Cell Line $IC_{50}$ (nM) | | |
|---|---|---|---|
| Compound | SKOV3 | SKVLB | Resistance Factor |
| Vinblastine | 0.35 ± 0.25 | 4200 ± 1700 | 12,000 |
| Taxol | 1 ± 0.4 | 8000 ± 2000 | 8,000 |
| Cryptophycins | 0.007 ± 0.002 | 0.60 ± 0.19 | 86 |

Thus it is demonstrated that the present invention provides novel cryptophycin compounds, as well as previously-disclosed cryptophycin compounds, which are potent inhibitors of cell proliferation, acting by disruption of the microtubule network and inhibition of mitosis. The cryptophycin compounds disrupt microtubule organization and thus normal cellular functions, including those of mitosis.

Classic anti-microtubule agents, such as colchicine and Vinca alkaloids, arrest cell division at mitosis. It seemed appropriate to compare the effect of one of these agents on cell proliferation with the cryptophycin compounds. For this purpose, the Vinca alkaloid vinblastine was selected as representative of the classic anti-microtubule agents. Accordingly, the effect of cryptophycin compounds and vinblastine on the proliferation and cell cycle progression of the Jurkat T-cell leukemia cell line was compared. Both compounds caused parallel dose-dependent inhibitions of cell proliferation and accumulation of cells in mitosis.

Since antimitotic effects are commonly mediated by disruption of microtubules in the mitotic spindles, the effects of cryptophycin compounds on cytoskeletal structures were characterized by fluorescence microscopy. Immunofluorescence staining of cells treated with either a cryptophycin compound or vinblastine clearly demonstrated that both compounds caused the complete loss of microtubules. Similar studies with SKOV3 cells demonstrate that the anti-microtubule effects of cryptophycin compounds are not unique to the smooth muscle cell line. Neither drug affected the levels or distribution of microfilament bundles, as was readily induced by cytochalasin B, indicating that the loss of microtubules may not be due to a non-specific mechanism, e.g. activation of proteases or loss of energy charge. Both vinblastine and cryptophycin compounds also promote marked collapse of vimentin intermediate filaments, such that brightly staining rings were formed around the cell nucleus.

Removal of vinblastine from the culture medium resulted in rapid repolymerization of microtubules. In contrast, cells treated with cryptophycin compounds remained depleted of microtubules for at least 24 hours after the compound was removed from the cultures.

The present invention demonstrates that cryptophycin compounds circumvent P-glycoprotein-mediated multiple drug resistance. Transport by Pglycoprotein limits the ability of natural product anticancer drugs to inhibit the growth of tumor cells with acquired or de novo drug resistance.[13–15] Vinca alkaloids, while very useful in the initial course of chemotherapy, are extremely good substrates for transport by P-glycoprotein, and so are of very limited usefulness against P-glycoprotein-mediated MDR tumors. Therefore, identification of agents which overcome multiple drug resistance may, should lead to the development of useful and novel anticancer agents. The cryptophycin compounds of the present invention appear to be such agents since they are poor substrates for P-glycoprotein-mediated transport. This fact is reflected in the low cell resistance factor for cryptophycin compounds compared with vinblastine, taxol and other natural product drugs.

All publications and patent applications cited in this specification, but not individually and specifically incorporated by reference, are herein incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the teaching of this invention that certain changes and modifications may be made thereto without departing from the spirit or scope of the claims.

References

1. Eglof, G., *Organic Chemistry: An Advanced Treatise*, Gilmar et al. (ed.), pp. 31–46, John Wiley & Sons (1943).
2. Kemp, et al., *Organic Chemistry*, Worth Publishers, Inc. (1980).
3. Patterson, G. M. L. et al. *J. Phycol.* 27:530-6 (1991).
4. Corbett, T. H. et al. *Cytotoxic Anticancer Drugs: Models and Concepts for Drug Discovery and Development*, pp 35–87; Kluwer Academic Publishers: Norwell, 1992.
5. Valeriote, F. A. et al. *Discovery and Development of Anticancer Agents*; Kluwer Academic Publishers: Norwell, 1993; in press.
6. Schwartz, R. E. et al. *J. Ind. Microbiol.* 5:113–24 (1990).
7. Hirsch, C. F. et al. U.S. Pat. No. 4,946,835, issued Aug. 7, 1990.
8. Sesin, D. F. U.S. Pat. No. 4,845,085, issued Jul. 4, 1989.
9. Sesin, D. F.; Liesch, J. M. U.S. Pat. No. 4,868,208, issued Sep. 19, 1989.
10. Sesin, D. F. U.S. Pat. No. 4,845,086, issued Jul. 4, 1989.
11. Skehan, P. et al., *J. Natl. Cancer Inst.* 82: 1107–1112 (1990).
12. Bradley, G. et al. *Cancer Res.* 49: 2790–2796 (1989).
13. Endicott, J. A. et al. *Ann. Rev. Biochem.* 58: 137–171 (1989).
14. Beck, W. T. *Biochem. Pharm.* 36: 2879–2887 (1987).
15. Moscow, J. A. et al. *J. Natl. Cancer Inst.* 80: 14–20 (1988).

What is claimed is:

1. A method for producing a compound having the ability to inhibit the proliferation of normal and hyperproliferative vertebrate cells; wherein said compound has the structure II as follows:

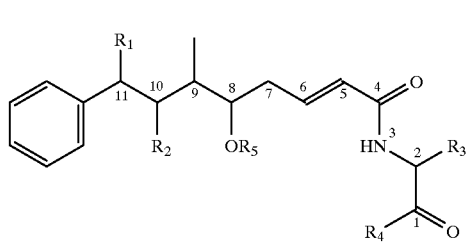

wherein:
  $R_1$ is H, OH, O of a ketone group, $NH_2$, SH, a lower alkoxyl group or a lower alkyl group;
  $R_2$ is H, OH, O of a ketone group, $NH_2$, SH, a lower alkoxyl group or a lower alkyl group; or
  $R_1$ and $R_2$ may be taken together to form an epoxide ring, an aziridine ring, a sulfide ring or a second bond between $C_{10}$ and $C_{11}$;
  $R_3$ is a benzyl, hydroxybenzyl, methoxybenzyl, halohydroxybenzyl or halomethoxybenzyl group;
  $R_4$ is OH, a lower δ-amino acid wherein $C_1$ is bonded to N of the δ-amino acid, or an esterified lower δ-amino acid wherein $C_1$ is bonded to N of the esterified lower δ-amino acid group; and
  $R_5$ is H, a lower alkanoyl group or a lower α-hydroxy alkanoyl group; or $R_4$ and $R_5$ may be taken together to form a didepsipeptide group consisting of a lower δ-amino acid bonded to a lower α-hydroxy alkanoic acid;
  with the following provisos:
  $R_1$ is H, a lower alkyl group, or a lower alkoxyl group only if $R_2$ is OH, O of a ketone group, $NH_2$, or SH; or
    $R_2$ is H, a lower alkyl group, or a lower alkoxyl group only if $R_1$ is OH, O of a ketone group, $NH_2$, or SH;
the method comprising:
  a) cultivating a culture of a Nostoc sp. designated GSV 224 (ATCC No. 55483);

b) isolating from the culture at least one compound having the structure II.

2. The method of claim 1 further comprising:
c) chemically modifying the compound obtained in step (b) to provide a compound having the structure II, wherein one or more of $R_1$, $R_2$, $R_3$, $R_4$ and $R_5$ differ relative to the metabolite isolated in step (b).

3. A method for producing a compound having the ability to inhibit the proliferation of normal and hyperproliferative vertebrate cells; said method comprising:
a) cultiyating a culture of Nostoc sp. designated GSV 224 (ATCC No. 55483);
b) isolatine from the culture a metabolite having the structure I as follows:

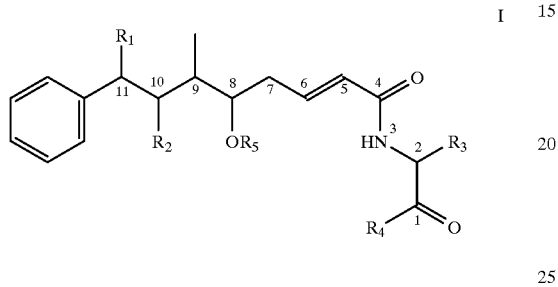

wherein:
$R_1$ is H, OH, O of a ketone group, $NH_2$, SH, a lower alkoxyl group or a lower alkyl group;
$R_2$ is H, OH, O of a ketone group, $NH_2$, SH, a lower alkoxyl group or a lower alkyl group; or

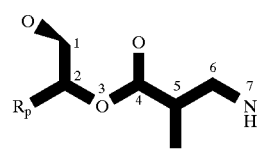

$R_1$ and $R_2$ may be taken together to form an epoxide ring, an aziridine ring, a sulfide ring or a second bond between $C_{10}$ and $C_{11}$;

$R_3$ is a benzyl, hydroxybenzrl, methoxybenzyl, halo-hydroxybenzyl or halomethoxybenzyl group;

R4 is OH, a lower 8-amino acid wherein $C_1$ is bonded to N of the 8-amino acid, or an esterified lower 8-arnino acid wherein $C_1$ is bonded to N of the esterified lower 8-amino acid group; and $R_5$ is H, a lower alkanoyl group or a lower a-hydroxy alkanoyl group; or $R_4$ and $R_3$ may be taken together to form a didepsipeptide group consisting of a lower 8amino acid bonded to a lower α-hydroxy alkanoic acid; and c) chemically modifying said metabolite by replacing $R_1$ with a halogen.

* * * * *

UNITED STATES PATENT AND TRADEMARK OFFICE
CERTIFICATE OF CORRECTION

PATENT NO. : 5,945,315
DATED : Aug. 31, 1999
INVENTOR(S) : Richard E. Moore and Gregory M. L. Patterson It is certified that error appears in the above-identified patent and that said Letters Patent is hereby corrected as shown below:

In claim 1, col. 30, lines 50, 51, 53, and 58 delete each occurrence of "8-amino" and substitute therefor --β-amino--.

In claim 3, col. 31, line 10, delete "cultiyating" and substitute therefor --cultivating--;
col. 31, line 12, delete "isolatine" and substitute therefor --isolating--;
col. 32, line 5, delete the structure depicted;
col. 32, line 13, delete "hydroxybenzrl" and substitute therefor --hydroxybenzyl--;
col. 32, line 16, delete "R4" and substitute therefor --R$_4$--;
col. 32, lines 16, 17, and 19 delete each occurrence of "8-amino" and substitute therefor --β-amino--;
col. 32, line 18, delete "8-arnino" and substitute therefor --β-amino--;
col. 32, line 20, delete "a-hydroxy" and substitute therefor --α-hydroxy--;
col. 32, line 22, delete "R$_3$" and substitute therefor --R$_5$--;
col. 32, line 23, delete "8amino" and substitute therefor --β-amino--.

Signed and Sealed this

Twenty-ninth Day of May, 2001

Attest:

NICHOLAS P. GODICI

Attesting Officer

Acting Director of the United States Patent and Trademark Office